(12) United States Patent
Park et al.

(10) Patent No.: US 8,993,343 B2
(45) Date of Patent: Mar. 31, 2015

(54) CD93 OR USE OF SOLUBLE FRAGMENT THEREOF

(75) Inventors: Young Woo Park, Daejon (KR); Jae Won Jeon, Daejeon (KR); Joon-Goo Jung, Daejeon (KR); Hye In Choi, Daejeon (KR); Myung-ho Sohn, Daejeon (KR); Ho youn Kim, Seoul (KR); Mi-La Cho, Seoul (KR); Young-Soon Jang, Daejeon (KR); Ji-Hun Moon, Daejeon (KR); Ji Hyun Park, Gyeongsangnam-do (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 286 days.

(21) Appl. No.: 13/146,876

(22) PCT Filed: Jan. 18, 2010

(86) PCT No.: PCT/KR2010/000315
§ 371 (c)(1),
(2), (4) Date: Oct. 11, 2011

(87) PCT Pub. No.: WO2010/087594
PCT Pub. Date: Aug. 5, 2010

(65) Prior Publication Data
US 2012/0039911 A1   Feb. 16, 2012

(30) Foreign Application Priority Data

Jan. 28, 2009 (KR) .......... 10-2009-0006592
Nov. 30, 2009 (KR) .......... 10-2009-0116723

(51) Int. Cl.
G01N 33/566 (2006.01)
G01N 33/53 (2006.01)
A61K 31/7105 (2006.01)
G01N 33/68 (2006.01)

(52) U.S. Cl.
CPC ........ *A61K 31/7105* (2013.01); *G01N 33/6893* (2013.01); *G01N 2333/70596* (2013.01)
USPC .......................................... 436/501; 436/548

(58) Field of Classification Search
None
See application file for complete search history.

(56) References Cited

U.S. PATENT DOCUMENTS 7,482,117 B2 * 1/2009 Cargill et al. ............. 435/6.14
2004/0101874 A1 * 5/2004 Ghosh et al. .................. 435/6

2006/0188951 A1 * 8/2006 Mook et al. ............... 435/7.92
2007/0026387 A1 * 2/2007 Ahearn et al. ................. 435/5
2011/0014608 A1 * 1/2011 Noorchashm et al. .......... 435/6

FOREIGN PATENT DOCUMENTS

WO    WO 9822584 A1 * 5/1998
WO    WO 2008082519 A2 * 7/2008

OTHER PUBLICATIONS

Quillen et al. "Diagnosing Rhinitis: Allergic vs. Nonallergic" aafp, 73(9), 2006, pp. 1583-1590.*
Friedman et al. (Immunoserology in the Diagnosis of Infectious Diseases, University Park Press, 1979, Chapter entitled "Radioimmunoassay and Enzyme Immunoassay" by Kenneith W. Walls, pp. 35-44).*
Crockard et al. "Increased expression of C1q receptors on neutrophils from inflammatory joint fluids" Immunology Letters, 36 (1993), 195-202.*
Bohlson et al. "CD93 is rapidly shed from the surface of human myeloid cells and the soluble form is detected in human plasma" J. Immunol 2005, 175, 1239-1247.*
Bohlson S. S. et al., "CD93 is rapidly shed from the surface of human myeloid cells and the soluble form is detected in human plasma", J. Immunol., Jul. 15, 2005, vol. 175, No. 2, pp. 1239-1247.
Norsworthy P. J. et al., "Murine CD93 (C1qRp) contributes to the removal of apoptotic cells in vivo but is not required for C1q-mediated enhancement of phagocytosis", J. Immunol., Mar. 15, 2004, vol. 172, No. 6, pp. 3406-3414.
Greenlee M. C. et al., "CD93 and related family members: their role in innate immunity", Curr Drug Targets, Feb. 2008, vol. 9, No. 2, pp. 130-138.
Ghebrehiwet B. et al., "cC1q-R (calreticulin) and gC1q-R/p33: ubiquitously expressed multi-ligand binding cellular proteins involved in inflammation and infection", Mol. Immunol., Jun. 2004, vol. 41, No. 2-3, pp. 173-183.
Greenlee M. C. et al., "Detection and characterization of soluble CD93 released during inflammation", Inflamm. Res., Jul. 15, 2009, vol. 58, pp. 909-919.
Jeon, J., et al., "Soluble CD93 induces differentiation of monocytes and enhances TLR responses", J. Immunol., Sep. 22, 2010, vol. 185, 000-000.
Malarstig, A., et al., "Plasma CD93 concentration is a potential novel biomarker for coronary artery disease", J. Int. Med., 2011, pp. 1365-2796.
ISA/KR, International Search Report of PCT/KR2010/000315 dated Aug. 26, 2010.

* cited by examiner

*Primary Examiner* — Daniel E Kolker
*Assistant Examiner* — James Rogers
(74) *Attorney, Agent, or Firm* — Lucas & Mercanti, LLP

(57) ABSTRACT

The present invention relates to an anti-inflammatory composition using the antibody specifically binding to CD93 or its soluble fragment, and a diagnostic method and a diagnostic kit for inflammatory disease using CD93 or its soluble fragment specific antibody or aptamer.

6 Claims, 25 Drawing Sheets

Fig. 1

A    SEQ ID NO: 3

```
  1 MATSMGLLLL LLLLLTQPGA GTGADTEAVV CVGTACYTAH SGKLSAAEAQ NHCNQNGGNL
 61 ATVKSKEEAQ HVQRVLAQLL RREAALTARM SKFWIGLQRE KGKCLDPSLP LKGFSWVGGG
121 EDTPYSNWHK ELRNSCISKR CVSLLLDLSQ PLLPSRLPKW SEGPCGSPGS PGSNIEGFVC
181 KFSFKGMCRP LALGGPGQVT YTTPFQTTSS SLEAVPFASA ANVACGEGDK DETQSHYFLC
241 KEKAPDVFDW GSSGPLCVSP KYGCNFNNGG CHQDCFEGGD GSFLCGCRPG FRLLDDLVTC
301 ASRNPCSSSP CRGGATCVLG PHGKNYTCRC PQGYQLDSSQ LDCVDVDECQ DSPCAQECVN
361 TPGGFRCECW VGYEPGGPGE GACQDVDECA LGRSPCAQGC TNTDGSFHCS CEEGYVLAGE
421 DGTQCQDVDE CVGPGGPLCD SLCFNTQGSF HCGCLPGWVL APNGVSCTMG PVSLGPPSGP
481 PDEEDKGEKE GSTVPRAATA SPTRGPEGTP KATPTTSRPS LSSDAPITSA PLKMLAPSGS
541 PGVWREPSIH HATAASGPQE PAGGDSSVAT QNNDGTDGQK LLLFYILGTV VAILLLLALA
601 LGLLVYRKRR AKREEKKEKK PQNAADSYSW VPERAESRAM ENQYSPTPGT DC
```

B    SEQ ID NO: 1

$^{21}$GTGADTEAVVCVGTACYTAHSGKLSAAEAQNHCNQNGGNLATVKSK
EEAQHVQRVLAQLLRREAALTARMSKFWIGLQREKGKCLDPSLPLKGFS
WVGGGEDTPYSNWHKELRNSCISKRCVSLLLDLSQPLLPSRLPKWSEGP
CGSPGSPGSNIEGFVCKFSFKGMCRPLALGGPGQVTYTTPFQTTSSSLEA
VPFASAANVACGEGDKDETQSHYFLCKEKAPDVFDWGSSGPLCVSPKY
GCNFNNGGCHQDCFEGGDGSFLCGCRPGFRLLDDLVTCASRNPCSSSP
CRGGATCVLGPHGKNYTCRCPQGYQLDSSQLDCVD$^{345}$

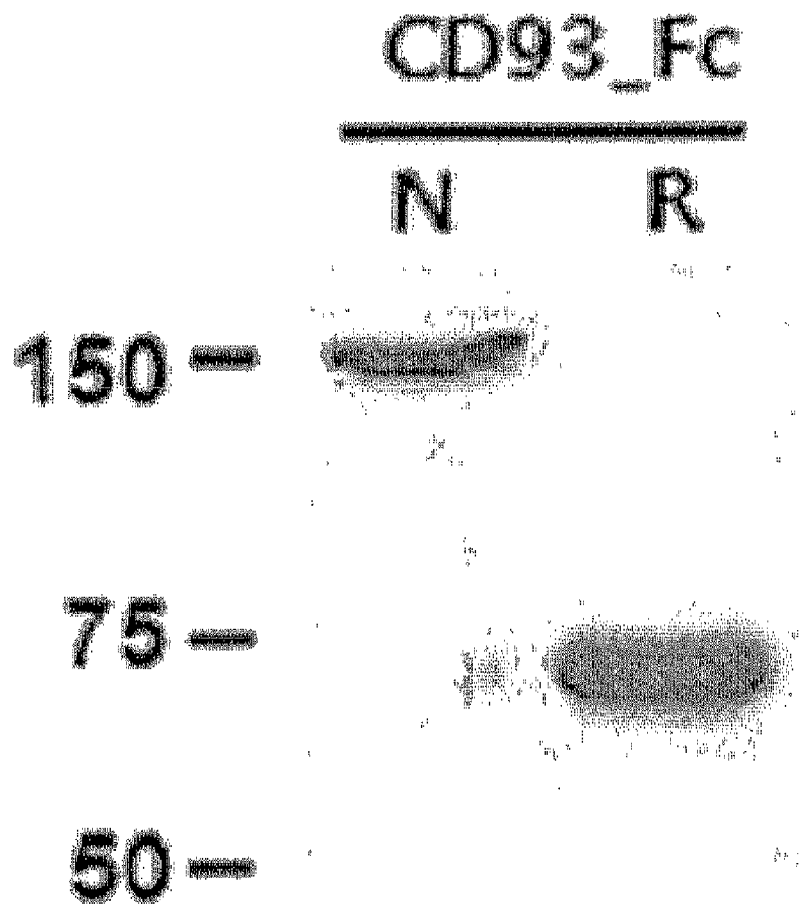

SEQUENCE LISTING

<160> NUMBER OF SEQ ID NOS: 37

<210> SEQ ID NO 1
<211> LENGTH: 325
<212> TYPE: PRT
<213> ORGANISM: Homo sapiens

<400> SEQUENCE: 1

Gly Thr Gly Ala Asp Thr Glu Ala Val Val Cys Val Gly Thr Ala Cys
1               5                   10                  15

Tyr Thr Ala His Ser Gly Lys Leu Ser Ala Ala Glu Ala Gln Asn His
            20                  25                  30

Cys Asn Gln Asn Gly Gly Asn Leu Ala Thr Val Lys Ser Lys Glu Glu
        35                  40                  45

Ala Gln His Val Gln Arg Val Leu Ala Gln Leu Leu Arg Arg Glu Ala
    50                  55                  60

Ala Leu Thr Ala Arg Met Ser Lys Phe Trp Ile Gly Leu Gln Arg Glu
65                  70                  75                  80

Lys Gly Lys Cys Leu Asp Pro Ser Leu Pro Leu Lys Gly Phe Ser Trp
                85                  90                  95

Val Gly Gly Gly Glu Asp Thr Pro Tyr Ser Asn Trp His Lys Glu Leu
            100                 105                 110

Arg Asn Ser Cys Ile Ser Lys Arg Cys Val Ser Leu Leu Asp Leu
            115                 120                 125

Ser Gln Pro Leu Leu Pro Ser Arg Leu Pro Lys Trp Ser Glu Gly Pro
    130                 135                 140

Cys Gly Ser Pro Gly Ser Pro Gly Ser Asn Ile Glu Gly Phe Val Cys
145                 150                 155                 160

Lys Phe Ser Phe Lys Gly Met Cys Arg Pro Leu Ala Leu Gly Gly Pro
                165                 170                 175

Gly Gln Val Thr Tyr Thr Thr Pro Phe Gln Thr Thr Ser Ser Ser Leu
            180                 185                 190

Glu Ala Val Pro Phe Ala Ser Ala Ala Asn Val Ala Cys Gly Glu Gly
            195                 200                 205

Asp Lys Asp Glu Thr Gln Ser His Tyr Phe Leu Cys Lys Glu Lys Ala
    210                 215                 220

Pro Asp Val Phe Asp Trp Gly Ser Ser Gly Pro Leu Cys Val Ser Pro
225                 230                 235                 240

Lys Tyr Gly Cys Asn Phe Asn Asn Gly Gly Cys His Gln Asp Cys Phe
                245                 250                 255

Glu Gly Gly Asp Gly Ser Phe Leu Cys Gly Cys Arg Pro Gly Phe Arg
            260                 265                 270

Leu Leu Asp Asp Leu Val Thr Cys Ala Ser Arg Asn Pro Cys Ser Ser
    275                 280                 285

Ser Pro Cys Arg Gly Gly Ala Thr Cys Val Leu Gly Pro His Gly Lys
    290                 295                 300

Asn Tyr Thr Cys Arg Cys Pro Gln Gly Tyr Gln Leu Asp Ser Ser Gln
305                 310                 315                 320

Leu Asp Cys Val Asp
            325

<210> SEQ ID NO 2
<211> LENGTH: 975
<212> TYPE: DNA
<213> ORGANISM: Homo sapiens

<400> SEQUENCE: 2

```
cccettgggg cccagctggg agccgagata gaagctcctg tcgccgctgg gcttctcgcc      60
tcccgcagag ggccacacag agaccgggat ggccacctcc atgggcctgc tgctgctgct     120
gctgctgctc ctgacccagc ccggggcggg gacgggagct gacacggagg cggtggtctg     180
cgtggggacc gcctgctaca cggcccactc gggcaagctg agcgctgccg aggcccagaa     240
ccactgcaac cagaacgggg gcaacctggc cactgtgaag agcaaggagg aggcccagca     300
cgtccagcga gtactggccc agctcctgag gcgggaggca gccctgacgg cgaggatgag     360
caagttctgg attgggctcc agcgagagaa gggcaagtgc ctggacccta gtctgccgct     420
gaagggcttc agctgggtgg gcggggggga ggacacgcct tactctaact ggcacaagga     480
gctccggaac tcgtgcatct ccaagcgctg tgtgtctctg ctgctggacc tgtcccagcc     540
gctccttccc agccgcctcc ccaagtggtc tgagggcccc tgtgggagcc caggctcccc     600
cggaagtaac attgagggct cgtgtgcaa gttcagcttc aaaggcatgt gccggcctct     660
ggccctgggg ggcccaggtc aggtgaccta caccaccccc ttccagacca ccagttcctc     720
cttggaggct gtgcccttg cctctgcggc caatgtagcc tgtggggaag gtgacaagga     780
cgagactcag agtcattatt tcctgtgcaa ggagaaggcc cccgatgtgt cgactgggg     840
cagctcgggc ccctctgtg tcagccccaa gtatggctgc aacttcaaca atggggctg      900
ccaccaggac tgctttgaag ggggggatgg ctccttcctc tgcggctgcc gaccaggatt     960
ccggctgctg gatga                                                     975
```

<210> SEQ ID NO 3
<211> LENGTH: 652
<212> TYPE: PRT
<213> ORGANISM: Homo sapiens

<400> SEQUENCE: 3

```
Met Ala Thr Ser Met Gly Leu Leu Leu Leu Leu Leu Leu Thr
 1               5                  10                  15

Gln Pro Gly Ala Gly Thr Gly Ala Asp Thr Glu Ala Val Val Cys Val
                20                  25                  30

Gly Thr Ala Cys Tyr Thr Ala His Ser Gly Lys Leu Ser Ala Ala Glu
            35                  40                  45

Ala Gln Asn His Cys Asn Gln Asn Gly Gly Asn Leu Ala Thr Val Lys
        50                  55                  60

Ser Lys Glu Glu Ala Gln His Val Gln Arg Val Leu Ala Gln Leu Leu
 65                  70                  75                  80

Arg Arg Glu Ala Ala Leu Thr Ala Arg Met Ser Lys Phe Trp Ile Gly
                85                  90                  95

Leu Gln Arg Glu Lys Gly Lys Cys Leu Asp Pro Ser Leu Pro Leu Lys
                100                 105                 110

Gly Phe Ser Trp Val Gly Gly Gly Glu Asp Thr Pro Tyr Ser Asn Trp
            115                 120                 125

His Lys Glu Leu Arg Asn Ser Cys Ile Ser Lys Arg Cys Val Ser Leu
        130                 135                 140

Leu Leu Asp Leu Ser Gln Pro Leu Leu Pro Ser Arg Leu Pro Lys Trp
145                 150                 155                 160

Ser Glu Gly Pro Cys Gly Ser Pro Gly Ser Pro Gly Ser Asn Ile Glu
                165                 170                 175

Gly Phe Val Cys Lys Phe Ser Phe Lys Gly Met Cys Arg Pro Leu Ala
            180                 185                 190
```

```
Leu Gly Gly Pro Gly Gln Val Thr Tyr Thr Thr Pro Phe Gln Thr Thr
            195                 200                 205

Ser Ser Ser Leu Glu Ala Val Pro Phe Ala Ser Ala Ala Asn Val Ala
        210                 215                 220

Cys Gly Glu Gly Asp Lys Asp Glu Thr Gln Ser His Tyr Phe Leu Cys
225                 230                 235                 240

Lys Glu Lys Ala Pro Asp Val Phe Asp Trp Gly Ser Ser Gly Pro Leu
                245                 250                 255

Cys Val Ser Pro Lys Tyr Gly Cys Asn Phe Asn Asn Gly Gly Cys His
                260                 265                 270

Gln Asp Cys Phe Glu Gly Gly Asp Gly Ser Phe Leu Cys Gly Cys Arg
            275                 280                 285

Pro Gly Phe Arg Leu Leu Asp Asp Leu Val Thr Cys Ala Ser Arg Asn
        290                 295                 300

Pro Cys Ser Ser Pro Cys Arg Gly Gly Ala Thr Cys Val Leu Gly
305                 310                 315                 320

Pro His Gly Lys Asn Tyr Thr Cys Arg Cys Pro Gln Gly Tyr Gln Leu
                325                 330                 335

Asp Ser Ser Gln Leu Asp Cys Val Asp Val Asp Glu Cys Gln Asp Ser
            340                 345                 350

Pro Cys Ala Gln Glu Cys Val Asn Thr Pro Gly Gly Phe Arg Cys Glu
        355                 360                 365

Cys Trp Val Gly Tyr Glu Pro Gly Gly Pro Gly Glu Gly Ala Cys Gln
370                 375                 380

Asp Val Asp Glu Cys Ala Leu Gly Arg Ser Pro Cys Ala Gln Gly Cys
385                 390                 395                 400

Thr Asn Thr Asp Gly Ser Phe His Cys Ser Cys Glu Glu Gly Tyr Val
                405                 410                 415

Leu Ala Gly Glu Asp Gly Thr Gln Cys Gln Asp Val Asp Glu Cys Val
            420                 425                 430

Gly Pro Gly Gly Pro Leu Cys Asp Ser Leu Cys Phe Asn Thr Gln Gly
        435                 440                 445

Ser Phe His Cys Gly Cys Leu Pro Gly Trp Val Leu Ala Pro Asn Gly
        450                 455                 460

Val Ser Cys Thr Met Gly Pro Val Ser Leu Gly Pro Pro Ser Gly Pro
465                 470                 475                 480

Pro Asp Glu Glu Asp Lys Gly Glu Lys Glu Gly Ser Thr Val Pro Arg
                485                 490                 495

Ala Ala Thr Ala Ser Pro Thr Arg Gly Pro Glu Gly Thr Pro Lys Ala
            500                 505                 510

Thr Pro Thr Thr Ser Arg Pro Ser Leu Ser Ser Asp Ala Pro Ile Thr
        515                 520                 525

Ser Ala Pro Leu Lys Met Leu Ala Pro Ser Gly Ser Pro Gly Val Trp
530                 535                 540

Arg Glu Pro Ser Ile His His Ala Thr Ala Ala Ser Gly Pro Gln Glu
545                 550                 555                 560

Pro Ala Gly Gly Asp Ser Ser Val Ala Thr Gln Asn Asn Asp Gly Thr
                565                 570                 575

Asp Gly Gln Lys Leu Leu Leu Phe Tyr Ile Leu Gly Thr Val Val Ala
            580                 585                 590

Ile Leu Leu Leu Leu Ala Leu Ala Leu Gly Leu Leu Val Tyr Arg Lys
        595                 600                 605
```

```
                Arg Arg Ala Lys Arg Glu Glu Lys Lys Glu Lys Lys Pro Gln Asn Ala
                    610                 615                 620

Ala Asp Ser Tyr Ser Trp Val Pro Glu Arg Ala Glu Ser Arg Ala Met
                625                 630                 635                 640

Glu Asn Gln Tyr Ser Pro Thr Pro Gly Thr Asp Cys
                                645                 650

<210> SEQ ID NO 4
<211> LENGTH: 6701
<212> TYPE: DNA
<213> ORGANISM: Homo sapiens

<400> SEQUENCE: 4
aaagccctca gcctttgtgt ccttctctgc gccggagtgg ctgcagctca ccctcagct      60 cccctttgggg cccagctggg agccgagata aagctcctg tcgccgctgg gcttctcgcc    120
tcccgcagag ggccacacag agaccgggat ggccacctcc atgggcctgc tgctgctgct   180
gctgctgctc ctgacccagc ccggggcggg acgggagct acacggagg cggtggtctg     240 cgtggggacc gcctgctaca cggcccactc gggcaagctg agcgctgccg aggcccagaa   300
ccactgcaac cagaacgggg gcaacctggc cactgtgaag agcaaggagg aggcccagca   360
cgtccagcga gtactggccc agctcctgag gcgggaggca gccctgacgg cgaggatgag   420
caagttctgg attgggctcc agcgagaaa gggcaagtgc ctggaccctc gtctgccgct   480
gaagggcttc agctgggtgg gcgggggga ggacacgcct tactctaact ggcacaagga   540
gctccggaac tcgtgcatct ccaagcgctg tgtgtctctg ctgctggacc tgtcccagcc   600
gctccttccc agccgcctcc ccaagtggtc tgagggcccc tgtgggagcc caggctcccc   660
cggaagtaac attgagggct tcgtgtgcaa gttcagcttc aaaggcatgt gccggcctct   720
ggccctgggg ggcccaggtc aggtgaccta caccaccccc ttccagacca ccagttcctc   780
cttggaggct gtgcccttg cctctgcggc aatgtagcc tgtggggaag gtgacaagga    840
cgagactcag agtcattatt tcctgtgcaa ggagaaggcc cccgatgtgt cgactgggg   900 cagctcgggc cccctctgtg tcagcccaa gtatggctgc aacttcaaca atggggctg    960 ccaccaggac tgctttgaag ggggggatgg ctccttcctc tgcggctgcc gaccaggatt   1020
ccggctgctg gatgacctgg tgacctgtgc ctctcgaaac ccttgcagct ccagcccatg   1080
tcgtgggggg gccacgtgcg tcctgggacc ccatgggaaa aactacacgt gccgctgccc   1140
ccaagggtac cagctggact cgagtcagct ggactgtgtg gacgtggatg aatgccagga   1200
ctccccctgt gccaggagt gtgtcaacac ccctgggggc ttccgctgcg aatgctgggt   1260
tggctatgag ccgggcggtc ctggagaggg ggcctgtcag gatgtggatg agtgtgctct   1320
gggtcgctcg ccttgcgccc agggctgcac caacacagat ggctcatttc actgctcctg   1380
tgaggagggc tacgtcctgg ccgggggaga cgggactcag tgccaggacg tggatgagtg   1440
tgtgggcccg gggggccccc tctgcgcacg cttgtgcttc aacacacaag gtccttcca    1500 ctgtggctgc ctgccaggct gggtgctggc cccaaatggg gtctcttgca ccatggggcc   1560
tgtgtctctg gaccaccat ctgggccccc cgatgaggag gacaaaggag agaaagaagg    1620
gagcaccgtg cccgtgctg caacagccag tcccacaagg ggcccgagg gcaccccaa     1680 ggctacaccc accacaagta gaccttcgct gtcatctgac gccccatca catctgcccc   1740 actcaagatg ctgccccca gtgggtcccc aggcgtctgg agggagccca gcatccatca   1800
cgccacagct gcctctggcc cccaggagcc tgcaggtggg gactcctccg tggccacaca   1860
```

```
aaacaacgat ggcactgacg ggcaaaagct gcttttattc tacatcctag gcaccgtggt    1920
ggccatccta ctcctgctgg ccctggctct ggggctactg gtctatcgca agcggagagc    1980
gaagagggag gagaagaagg agaagaagcc ccagaatgcg gcagacagtt actcctgggt    2040
tccagagcga gctgagagca gggccatgga gaaccagtac agtccgacac ctgggacaga    2100
ctgctgaaag tgaggtggcc ctagagacac tagagtcacc agccaccatc ctcagagctt    2160
tgaactcccc attccaaagg ggcacccaca ttttttgaa agactggact ggaatcttag     2220
caaacaattg taagtctcct ccttaaaggc cccttggaac atgcaggtat tttctacggg    2280
tgtttgatgt tcctgaagtg gaagctgtgt gttggcgtgc cacggtgggg atttcgtgac    2340
tctataatga ttgttactcc ccctcccttt tcaaattcca atgtgaccaa ttccggatca    2400
gggtgtgagg aggccgggc taaggggctc ccctgaatat cttctctgct cacttccacc     2460
atctaagagg aaaaggtgag ttgctcatgc tgattaggat tgaaatgatt tgtttctctt    2520
cctaggatga aaactaaatc aattaattat tcaattaggt aagaagatct ggttttttgg    2580
tcaaagggaa catgttcgga ctggaaacat ttctttacat ttgcattcct ccatttcgcc    2640
agcacaagtc ttgctaaatg tgatactgtt gacatcctcc agaatggcca gaagtgcaat    2700
taacctctta ggtggcaagg aggcaggaag tgcctcttta gttcttacat ttctaatagc    2760 cttgggtttta tttgcaaagg aagcttgaaa aatatgagaa aagttgcttg aagtgcatta    2820
caggtgtttg tgaagtcaca taatctacgg ggctagggcg agagaggcca gggatttgtt    2880
cacagatact tgaattaatt catccaaatg tactgaggtt accacacact tgactacgga    2940
tgtgatcaac actaacaagg aaacaaattc aaggacaacc tgtctttgag ccagggcagg    3000
cctcagacac cctgcctgtg gccccgcctc cacttcatcc tgcccggaat gccagtgctc    3060
cgagctcaga cagaggaagc cctgcagaaa gttccatcag gctgtttcct aaaggatgtg    3120
tgaacgggag atgatgcact gtgttttgaa agttgtcatt ttaaagcatt ttagcacagt    3180
tcatagtcca cagttgatgc agcatcctga gattttaaat cctgaagtgt gggtggcgca    3240
cacaccaagt agggagctag tcaggcagtt tgcttaagga acttttgttc tctgtctctt    3300
ttccttaaaa ttgggggtaa ggagggaagg aagagggaaa gagatgacta actaaaatca    3360
tttttacagc aaaaactgct caaagccatt taaattatat cctcatttta aaagttacat    3420
ttgcaaatat ttctccctat gataatgtag tcgatagtgt gcactctttc tctctctctc    3480
tctctctcac acacacacac acacacacac acacacacac agagacacgg caccattctg    3540
cctggggcac tggaacacat tcctgggggt caccgatggt cagagtcact agaagttacc    3600
tgagtatctc tgggaggcct catgtctcct gtgggctttt taccaccact gtgcaggaga    3660
acagacagag gaaatgtgtc tccctccaag gccccaaagc ctcagagaaa gggtgtttct    3720
ggttttgcct tagcaatgca tcggtctctg aggtgacact ctggagtggt tgaagggcca    3780
caaggtgcag ggttaatact cttgccagtt ttgaaatata gatgctatgg ttcagattgt    3840
ttttaataga aaactaaagg ggcagggaa gtgaaaggaa agatgaggt tttgtgcggc     3900 tcgatggggc atttggaact tcttttttaaa gtcatctcat ggtctccagt tttcagttgg    3960
aactctggtg tttaacactt aagggagaca aaggctgtgt ccatttggca aaacttcctt    4020
ggccacgaga ctctaggtga tgtgtgaagc tgggcagtct gtggtgtgga gagcagccat    4080
ctgtctggcc attcagagga ttctaaagac atggctggat gcgctgctga ccaacatcag    4140
cacttaaata aatgcaaatg caacatttct ccctctgggc cttgaaaatc cttgccctta    4200
tcatttgggg tgaaggagac atttctgtcc ttggcttccc acagccccaa cgcagtctgt    4260
```

```
gtatgattcc tgggatccaa cgagccctcc tattttcaca gtgttctgat tgctctcaca    4320
gcccaggccc atcgtctgtt ctctgaatgc agccctgttc tcaacaacag ggaggtcatg    4380
gaacccctct gtggaaccca caaggggaga atgggtgat aaagaatcca gttcctcaaa     4440
accttccctg gcaggctggg tccctctcct gctgggtggt gctttctctt gcacaccact    4500
cccaccacgg ggggagagcc agcaacccaa ccagacagct caggttgtgc atctgatgga    4560
aaccactggg ctcaaacacg tgctttattc tcctgtttat ttttgctgtt actttgaagc    4620
atggaaattc ttgtttgggg gatcttgggg ctacagtagt gggtaaacaa atgcccaccg    4680
gccaagaggc cattaacaaa tcgtccttgt cctgaggggc cccagcttgc tcgggcgtgg    4740
cacagtgggg aatccaaggg tcacagtatg gggagaggtg caccctgcca cctgctaact    4800
tctcgctaga cacagtgttt ctgcccaggt gacctgttca gcagcagaac aagccagggc    4860
catggggacg ggggaagttt tcacttggag atggacacca agacaatgaa gatttgttgt    4920
ccaaataggt caataattct gggagactct tggaaaaaac tgaatatatt caggaccaac    4980
tctctccctc ccctcatccc acatctcaaa gcagacaatg taaagagaga acatctcaca    5040
cacccagctc gccatgccta ctcattcctg aatttcaggt gccatcactg ctctttcttt    5100
cttctttgtc atttgagaaa ggatgcagga ggacaattcc cacagataat ctgaggaatg    5160
cagaaaaacc agggcaggac agttatcgac aatgcattag aacttggtga gcatcctctg    5220
tagagggact ccaccccctgc tcaacagctt ggcttccagg caagaccaac cacatctggt    5280
ctctgccttc ggtggcccac acacctaagc gtcatcgtca ttgccatagc atcatgatgc    5340
aacacatcta cgtgtagcac tacgacgtta tgtttgggta atgtggggat gaactgcatg    5400
aggctctgat taaggatgtg gggaagtggg ctgcggtcac tgtcggcctt gcaaggccac    5460
ctggaggcct gtctgttagc cagtggtgga ggagcaaggc ttcaggaagg gccagccaca    5520
tgccatcttc cctgcgatca ggcaaaaaag tggaattaaa aagtcaaacc tttatatgca    5580
tgtgttatgt ccattttgca ggatgaactg agtttaaaag aatttttttt tctcttcaag    5640
ttgctttgtc ttttccatcc tcatcacaag cccttgtttg agtgtcttat ccctgagcaa    5700
tctttcgatg gatggagatg atcattaggt acttttgttt caacctttat tcctgtaaat    5760
atttctgtga aaactaggag aacagagatg agatttgaca aaaaaaaatt gaattaaaaa    5820
taacacagtc ttttttaaaac taacatagga aagccttttcc tattatttct cttcttagct    5880
tctccattgt ctaaatcagg aaaacaggaa aacacagctt tctagcagct gcaaaatggt    5940
ttaatgcccc ctacatattt ccatcacctt gaacaatagc tttagcttgg gaatctgaga    6000
tatgatccca gaaacatctg tctctactt cggctgcaaa acccatggtt taaatctata    6060
tggtttgtgc attttctcaa ctaaaaatag agatgataat ccgaattctc catatattca    6120
ctaatcaaag acactatttt catactagat tcctgagaca aatactcact gaagggcttg    6180
tttaaaaata aattgtgttt tggtctgttc ttgtagataa tgcccttcta ttttaggtag    6240
aagctctgga atccctttat tgtgctgttg ctcttatctg caaggtggca agcagttctt    6300
ttcagcagat tttgcccact attcctctga gctgaagttc tttgcataga tttggcttaa    6360
gcttgaatta gatccctgca aaggcttgct ctgtgatgtc agatgtaatt gtaaatgtca    6420
gtaatcactt catgaatgct aaatgagaat gtaagtattt ttaaatgtgt gtatttcaaa    6480
tttgtttgac taattctgga attacaagat ttctatgcag gatttacctt catcctgtgc    6540
atgtttccca aactgtgagg agggaaggct cagagatcga gcttctcctc tgagttctaa    6600
```

```
caaaatggtg ctttgagggt cagcctttag gaaggtgcag ctttgttgtc ctttgagctt    6660
tctgttatgt gcctatccta ataaactctt aaacacattg a                        6701
```

<210> SEQ ID NO 5
<211> LENGTH: 22
<212> TYPE: DNA
<213> ORGANISM: Artificial Sequence
<220> FEATURE:
<223> OTHER INFORMATION: CD14-New forward primer

<400> SEQUENCE: 5

```
gcctagacct cagccacaac tc                                             22
```

<210> SEQ ID NO 6
<211> LENGTH: 19
<212> TYPE: DNA
<213> ORGANISM: Artificial Sequence
<220> FEATURE:
<223> OTHER INFORMATION: CD14-New reverse primer

<400> SEQUENCE: 6

```
ccagcccagc gaacgacag                                                 19
```

<210> SEQ ID NO 7
<211> LENGTH: 21
<212> TYPE: DNA
<213> ORGANISM: Artificial Sequence
<220> FEATURE:
<223> OTHER INFORMATION: CD64-New forward primer

<400> SEQUENCE: 7

```
gggtcagcgt gttccaagag g                                              21
```

<210> SEQ ID NO 8
<211> LENGTH: 25
<212> TYPE: DNA
<213> ORGANISM: Artificial Sequence
<220> FEATURE:
<223> OTHER INFORMATION: CD64-New reverse primer

<400> SEQUENCE: 8

```
gcacctgtat tcaccactgt cattg                                          25
```

<210> SEQ ID NO 9
<211> LENGTH: 21
<212> TYPE: DNA
<213> ORGANISM: Artificial Sequence
<220> FEATURE:
<223> OTHER INFORMATION: CD1a-New forward primer

<400> SEQUENCE: 9

```
actcatacct gggacagcaa t                                              21
```

<210> SEQ ID NO 10
<211> LENGTH: 21
<212> TYPE: DNA
<213> ORGANISM: Artificial Sequence
<220> FEATURE:
<223> OTHER INFORMATION: CD1a-New reverse primer

<400> SEQUENCE: 10

```
ctgcaattca tgggcgtatc t                                              21
```

<210> SEQ ID NO 11
<211> LENGTH: 21

```
<212> TYPE: DNA
<213> ORGANISM: Artificial Sequence
<220> FEATURE:
<223> OTHER INFORMATION: IL-6 forward primer

<400> SEQUENCE: 11
tggctgaaaa agatggatgc t                                             21

<210> SEQ ID NO 12
<211> LENGTH: 21
<212> TYPE: DNA
<213> ORGANISM: Artificial Sequence
<220> FEATURE:
<223> OTHER INFORMATION: IL-6 reverse primer

<400> SEQUENCE: 12
tctggcttgt tcctcactac t                                             21

<210> SEQ ID NO 13
<211> LENGTH: 21
<212> TYPE: DNA
<213> ORGANISM: Artificial Sequence
<220> FEATURE:
<223> OTHER INFORMATION: IL-12 forward primer

<400> SEQUENCE: 13
tgtaccaggt ggagttcaag a                                             21

<210> SEQ ID NO 14
<211> LENGTH: 21
<212> TYPE: DNA
<213> ORGANISM: Artificial Sequence
<220> FEATURE:
<223> OTHER INFORMATION: IL-12 reverse primer

<400> SEQUENCE: 14
ggaggatttt tgtggcacag t                                             21

<210> SEQ ID NO 15
<211> LENGTH: 21
<212> TYPE: DNA
<213> ORGANISM: Artificial Sequence
<220> FEATURE:
<223> OTHER INFORMATION: iNOS forward primer

<400> SEQUENCE: 15
atcttgcctg gggtccatta t                                             21

<210> SEQ ID NO 16
<211> LENGTH: 21
<212> TYPE: DNA
<213> ORGANISM: Artificial Sequence
<220> FEATURE:
<223> OTHER INFORMATION: iNOS reverse primer

<400> SEQUENCE: 16
cctggccaga tgttcctcta t                                             21

<210> SEQ ID NO 17
<211> LENGTH: 21
<212> TYPE: DNA
<213> ORGANISM: Artificial Sequence
<220> FEATURE:
<223> OTHER INFORMATION: CXCL11 forward primer

<400> SEQUENCE: 17
```
cctggggtaa aagcagtgaa a                                            21

<210> SEQ ID NO 18
<211> LENGTH: 21
<212> TYPE: DNA
<213> ORGANISM: Artificial Sequence
<220> FEATURE:
<223> OTHER INFORMATION: CXCL11 reverse primer

<400> SEQUENCE: 18
ttgcttgctt cgatttggga t                                            21

<210> SEQ ID NO 19
<211> LENGTH: 21
<212> TYPE: DNA
<213> ORGANISM: Artificial Sequence
<220> FEATURE:
<223> OTHER INFORMATION: CLEC4A forward primer

<400> SEQUENCE: 19
ttggcaagac agtgagaagg a                                            21

<210> SEQ ID NO 20
<211> LENGTH: 21
<212> TYPE: DNA
<213> ORGANISM: Artificial Sequence
<220> FEATURE:
<223> OTHER INFORMATION: CLEC4A reverse primer

<400> SEQUENCE: 20
aatgtcgctg accttctgga t                                            21

<210> SEQ ID NO 21
<211> LENGTH: 21
<212> TYPE: DNA
<213> ORGANISM: Artificial Sequence
<220> FEATURE:
<223> OTHER INFORMATION: SPHK-1 forward primer

<400> SEQUENCE: 21
ctgtaggaag agtgggttcc a                                            21

<210> SEQ ID NO 22
<211> LENGTH: 20
<212> TYPE: DNA
<213> ORGANISM: Artificial Sequence
<220> FEATURE:
<223> OTHER INFORMATION: SPHK-1 reverse primer

<400> SEQUENCE: 22
gtgccaggac tagcacaaag                                              20

<210> SEQ ID NO 23
<211> LENGTH: 21
<212> TYPE: DNA
<213> ORGANISM: Artificial Sequence
<220> FEATURE:
<223> OTHER INFORMATION: IL-1 beta forward primer

<400> SEQUENCE: 23
acagctggag agtgtagatc c                                            21

<210> SEQ ID NO 24
<211> LENGTH: 21
<212> TYPE: DNA
<213> ORGANISM: Artificial Sequence -continued

```
<220> FEATURE:
<223> OTHER INFORMATION: IL-1 beta reverse primer

<400> SEQUENCE: 24
ttttctgctt gagaggtgct g                                            21

<210> SEQ ID NO 25
<211> LENGTH: 21
<212> TYPE: DNA
<213> ORGANISM: Artificial Sequence
<220> FEATURE:
<223> OTHER INFORMATION: TNF-alpha forward primer

<400> SEQUENCE: 25
tagcccatgt tgtagcaaac c                                            21

<210> SEQ ID NO 26
<211> LENGTH: 21
<212> TYPE: DNA
<213> ORGANISM: Artificial Sequence
<220> FEATURE:
<223> OTHER INFORMATION: TNF-alpha reverse primer

<400> SEQUENCE: 26
agaggacctg ggagtagatg a                                            21

<210> SEQ ID NO 27
<211> LENGTH: 25
<212> TYPE: DNA
<213> ORGANISM: Artificial Sequence
<220> FEATURE:
<223> OTHER INFORMATION: pMEP4 forward primer

<400> SEQUENCE: 27
gtagatctgc aggaaaagga caagc                                        25

<210> SEQ ID NO 28
<211> LENGTH: 26
<212> TYPE: DNA
<213> ORGANISM: Artificial Sequence
<220> FEATURE:
<223> OTHER INFORMATION: pMEP4 reverse primer

<400> SEQUENCE: 28
cgagatctgg ttgacttccc taatgt                                       26

<210> SEQ ID NO 29
<211> LENGTH: 40
<212> TYPE: DNA
<213> ORGANISM: Artificial Sequence
<220> FEATURE:
<223> OTHER INFORMATION: Bam HI SfiI human immunoglobulin Fc N terminal
      sequence forward primer

<400> SEQUENCE: 29
cgggatccgg ccgtgggggc cgacaaaact cacacatgcc                        40

<210> SEQ ID NO 30
<211> LENGTH: 27
<212> TYPE: DNA
<213> ORGANISM: Artificial Sequence
<220> FEATURE:
<223> OTHER INFORMATION: XbaI stop codon human immunoglobulin Fc C
      terminal sequence reverse primer

<400> SEQUENCE: 30
```
cgagtctcat ttacccggag acaggga                                              27

<210> SEQ ID NO 31
<211> LENGTH: 38
<212> TYPE: DNA
<213> ORGANISM: Artificial Sequence
<220> FEATURE:
<223> OTHER INFORMATION: CD93 plasmid forward primer

<400> SEQUENCE: 31 caggggccg tgggggccac gggagctgac acggaggc                                   38

<210> SEQ ID NO 32
<211> LENGTH: 39
<212> TYPE: DNA
<213> ORGANISM: Artificial Sequence
<220> FEATURE:
<223> OTHER INFORMATION: CD93 plasmid reverse primer

<400> SEQUENCE: 32
tagcggccga cgcggccaag tccacacagt ccagctgac                                 39

<210> SEQ ID NO 33
<211> LENGTH: 652
<212> TYPE: PRT
<213> ORGANISM: Homo sapiens

<400> SEQUENCE: 33

Met Ala Thr Ser Met Gly Leu Leu Leu Leu Leu Leu Leu Leu Leu Thr
1               5                   10                  15

Gln Pro Gly Ala Gly Thr Gly Ala Asp Thr Glu Ala Val Val Cys Val
                20                  25                  30

Gly Thr Ala Cys Tyr Thr Ala His Ser Gly Lys Leu Ser Ala Ala Glu
            35                  40                  45

Ala Gln Asn His Cys Asn Gln Asn Gly Gly Asn Leu Ala Thr Val Lys
        50                  55                  60

Ser Lys Glu Glu Ala Gln His Val Gln Arg Val Leu Ala Gln Leu Leu
65                  70                  75                  80

Arg Arg Glu Ala Ala Leu Thr Ala Arg Met Ser Lys Phe Trp Ile Gly
                85                  90                  95

Leu Gln Arg Glu Lys Gly Lys Cys Leu Asp Pro Ser Leu Pro Leu Lys
                100                 105                 110

Gly Phe Ser Trp Val Gly Gly Gly Glu Asp Thr Pro Tyr Ser Asn Trp
            115                 120                 125

His Lys Glu Leu Arg Asn Ser Cys Ile Ser Lys Arg Cys Val Ser Leu
        130                 135                 140

Leu Leu Asp Leu Ser Gln Pro Leu Leu Pro Ser Arg Leu Pro Lys Trp
145                 150                 155                 160

Ser Glu Gly Pro Cys Gly Ser Pro Gly Ser Pro Gly Ser Asn Ile Glu
                165                 170                 175

Gly Phe Val Cys Lys Phe Ser Phe Lys Gly Met Cys Arg Pro Leu Ala
                180                 185                 190

Leu Gly Gly Pro Gly Gln Val Thr Tyr Thr Thr Pro Phe Gln Thr Thr
            195                 200                 205

Ser Ser Ser Leu Glu Ala Val Pro Phe Ala Ser Ala Ala Asn Val Ala
        210                 215                 220

Cys Gly Glu Gly Asp Lys Asp Glu Thr Gln Ser His Tyr Phe Leu Cys
225                 230                 235                 240

```
Lys Glu Lys Ala Pro Asp Val Phe Asp Trp Gly Ser Gly Pro Leu
                245                 250                 255
Cys Val Ser Pro Lys Tyr Gly Cys Asn Phe Asn Asn Gly Gly Cys His
            260                 265                 270
Gln Asp Cys Phe Glu Gly Gly Asp Gly Ser Phe Leu Cys Gly Cys Arg
        275                 280                 285
Pro Gly Phe Arg Leu Leu Asp Asp Leu Val Thr Cys Ala Ser Arg Asn
    290                 295                 300
Pro Cys Ser Ser Ser Pro Cys Arg Gly Gly Ala Thr Cys Val Leu Gly
305                 310                 315                 320
Pro His Gly Lys Asn Tyr Thr Cys Arg Cys Pro Gln Gly Tyr Gln Leu
                325                 330                 335
Asp Ser Ser Gln Leu Asp Cys Val Asp Val Asp Glu Cys Gln Asp Ser
            340                 345                 350
Pro Cys Ala Gln Glu Cys Val Asn Thr Pro Gly Gly Phe Arg Cys Glu
        355                 360                 365
Cys Trp Val Gly Tyr Glu Pro Gly Gly Pro Gly Glu Gly Ala Cys Gln
    370                 375                 380
Asp Val Asp Glu Cys Ala Leu Gly Arg Ser Pro Cys Ala Gln Gly Cys
385                 390                 395                 400
Thr Asn Thr Asp Gly Ser Phe His Cys Ser Cys Glu Glu Gly Tyr Val
                405                 410                 415
Leu Ala Gly Glu Asp Gly Thr Gln Cys Gln Asp Val Asp Glu Cys Val
            420                 425                 430
Gly Pro Gly Gly Pro Leu Cys Asp Ser Leu Cys Phe Asn Thr Gln Gly
        435                 440                 445
Ser Phe His Cys Gly Cys Leu Pro Gly Trp Val Leu Ala Pro Asn Gly
    450                 455                 460
Val Ser Cys Thr Met Gly Pro Val Ser Leu Gly Pro Pro Ser Gly Pro
465                 470                 475                 480
Pro Asp Glu Glu Asp Lys Gly Glu Lys Glu Gly Ser Thr Val Pro Arg
                485                 490                 495
Ala Ala Thr Ala Ser Pro Thr Arg Gly Pro Glu Gly Thr Pro Lys Ala
            500                 505                 510
Thr Pro Thr Thr Ser Arg Pro Ser Leu Ser Ser Asp Ala Pro Ile Thr
        515                 520                 525
Ser Ala Pro Leu Lys Met Leu Ala Pro Ser Gly Ser Pro Gly Val Trp
    530                 535                 540
Arg Glu Pro Ser Ile His His Ala Thr Ala Ala Ser Gly Pro Gln Glu
545                 550                 555                 560
Pro Ala Gly Gly Asp Ser Ser Val Ala Thr Gln Asn Asn Asp Gly Thr
                565                 570                 575
Asp Gly Gln Lys Leu Leu Leu Phe Tyr Ile Leu Gly Thr Val Val Ala
            580                 585                 590
Ile Leu Leu Leu Leu Ala Leu Ala Leu Gly Leu Leu Val Tyr Arg Lys
        595                 600                 605
Arg Arg Ala Lys Arg Glu Glu Lys Glu Lys Lys Pro Gln Asn Ala
    610                 615                 620
Ala Asp Ser Tyr Ser Trp Val Pro Glu Arg Ala Glu Ser Arg Ala Met
625                 630                 635                 640
Glu Asn Gln Tyr Ser Pro Thr Pro Gly Thr Asp Cys
                645                 650
```

```
<210> SEQ ID NO 34
<211> LENGTH: 21
<212> TYPE: DNA
<213> ORGANISM: Artificial Sequence
<220> FEATURE:
<223> OTHER INFORMATION: CD93 forward primer

<400> SEQUENCE: 34
ctctggggct actggtctat c                                              21

<210> SEQ ID NO 35
<211> LENGTH: 21
<212> TYPE: DNA
<213> ORGANISM: Artificial Sequence
<220> FEATURE:
<223> OTHER INFORMATION: CD93 reverse prime

<400> SEQUENCE: 35
tgtcggactg tactggttct c                                              21

<210> SEQ ID NO 36
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 36
catgttcgtc atgggtgtga a                                              21

<210> SEQ ID NO 37
<211> LENGTH: 21
<212> TYPE: DNA
<213> ORGANISM: Artificial Sequence
<220> FEATURE:
<223> OTHER INFORMATION: GAPDH reverse primer

<400> SEQUENCE: 37
ggactgtggt catgagtcct t                                              21
```

CD93 OR USE OF SOLUBLE FRAGMENT THEREOF

CROSS-REFERENCE TO RELATED APPLICATIONS

This application is a 371 of PCT/KR2010/000315 filed on Jan. 18, 2010, which claims the benefit of Korean Patent Application Nos. 10-2009-0116723 filed Nov. 30, 2009, and 10-2009-0006592 filed Jan. 28, 2009, the contents of each of which are incorporated herein by reference.

BACKGROUND OF THE INVENTION

1. Field of the Invention

The present invention relates to an anti-inflammatory composition, a diagnostic method and a diagnostic kit for inflammatory disease prepared by using antibody specifically binding to CD93 or soluble fragment of the same.

2. Description of the Related Art

Human CD93 (C1qRp, AA4.1(mouse)) is type 1 transmembrane glycoprotein located on chromosome 20, p11.21 (Malhotra, R. et al., 1993. *Immunology* 78: 341-348; Nepomuceno, R. R. et al., 1997. *Immunity* 6: 119-129; Steinberger, P. et al., 2002. *Biol.* 71: 133-140). According to the previous reports, this protein is involved in cell-cell interaction during B cell development and phagocytosis (Petrenko, O. et al., 1999. *Immunity* 10: 691-700; Norsworthy, P. J. et al., 2004. *J. Immunol.* 172: 3406-3414; Nepomuceno, R. R. et al., 1997. *Immunity* 6: 119-129; McGreal, E. P. et al., 2002. *J. Immunol.* 168: 5222-5232).

CD93 is composed of 652 amino acids including leader sequence, c-type carbohydrate-sensing domain, 5 EGF-like domains, mucin domain, one transmembrane domain, and intracellular domain of 47 amino acids (Nepomuceno R. R. et al., 1997. *Immunity* 6:119-129; Park, M. et al., 2003. *J. Cell Physiol.* 196: 512-522; Nepomuceno, R. R. et al., *J. Immunol.* 162:3583). CD93 is expressed in myeloid lineages, hematopoietic stem cells, NK cells, platelets, microglia, and endothelial cells, etc (Nepomuceno, R. R. et al., 1997. *Immunity* 6:119; Nepomuceno, R. R. et al., 1998. *J. Immunol.* 160: 1929; Danet G. H. et al., *Proc Natl Acad Sci USA* 2002; 99:10441-5; Lovik G. et al., *J Immunol* 2000; 30:3355-62; Fonseca M. I. et al., *J Leukoc Biol* 2001; 70:793-800; Webster, S. D. et al., 2000. *J. Leukocyte Biol.* 67:109). A previous report stated that CD93 was not expressed in tissue macrophages but expressed in vascular endothelial cells in a large scale (Petrenko, O. et al., 1999. *Immunity* 10:691; Dean, Y. D. et al., *J. Immunol.* 31:1370; Fonseca, M. I. et al., 2001. *J. Leukocyte Biol.* 70:793.). CD93 was presumed to be involved in C1q-mediated enhancement of phagocytosis, according to a research using anti-CD93 antibody, suggesting that CD93 might be acting as C1q receptor. However, consequent experiments proved that CD93 did not bind directly to C1q (Nepomuceno, R. R. et al. 1999. *J. Immunol.* 162:3583; McGreal, E. P. et al., 2002. *J. Immunol.* 168:5222; Steinberger, P. et al., 2002. *J. Leukocyte Biol.* 71:133).

In the experiment with CD93 knock-out mouse, a problem in eliminating killed cells was caused by the absence of CD93. However, in the in vitro experiment, no functional abnormality was observed (Guan, E. et al., 1994. *J. Immunol.* 152: 4005-4016; Norsworthy, P. J. et al., 2004. *J. Immunol.* 172: 3406-3414; Norsworthy, P. J. et al., 2004. *J. Immunol.* 172: 3406-3414). Phagocytosis plays an important role in the early stage of immune response, that is the function is very important in eliminating killed cells (Brown, E. J. (1995) Phagocytosis. *Bioessays* 17, 109-117).

Recent studies provided some clues to answer the questions about such functions. For example, it has been reported that shedding of CD93 occurs in the pro-inflammatory state of TNF-α and LPS, etc., so that ectodomain of CD93 is cut off (Park, M. et al., 2003. *J. Cell Physiol.* 196: 512-522.; Suzanne S. Bohlson et al., 2005. *J. immunol.* 175: 1239-1247). It has also been reported that CD93 is fragmentized into soluble fragments in U937 cells by the treatment of PMA (phorbol-12-myristate-13-acetate) (Ikewaki N., Tamauchi H., and Inoko H. 2007. Decrease in CD93 expression in a human monocyte-like cell line (U937) treated with various apoptosis-inducing chemical substances. Microbiol. Immunol., 51(12):1189-1200). Besides, WO 2008/082519 states that CD93-related polymorphs are very useful for the diagnosis of type-1 diabetes and Lupus Erythematosus. However, there have no reports made yet about the use of CD93 for the treatment or diagnosis of inflammatory disease.

Thus, the present inventors studied the possibility of the involvement of CD93 or its soluble fragment in inflammation. As a result, the present inventors confirmed that a soluble fragment of CD93 has excellent anti-inflammatory effect and CD93 or its soluble fragment is over-expressed in the presence of inflammation inducing substances or inflammatory environment, so that the inventors further completed this invention by proving that a soluble fragment of CD3 can be used as an active ingredient of an anti-inflammatory composition and CD93 or a soluble fragment thereof can also be used as a diagnostic marker for inflammatory disease.

SUMMARY OF THE INVENTION

It is an object of the present invention to provide an anti-inflammatory composition prepared by using soluble fragment of CD93.

It is another object of the present invention to provide a diagnostic kit for inflammatory disease and a diagnostic method for inflammatory disease using CD93 or soluble fragment of the same.

To achieve the above objects, the present invention provides an anti-inflammatory composition containing antibody specific to the soluble fragment of CD93 composed of the amino acid sequence represented by SEQ. ID. NO: 1 as an active ingredient.

The present invention also provides an anti-inflammatory composition containing one or more substances selected from the group consisting of siRNA, shRNA, and shRNA expression vector capable of suppressing the expression of CD93 gene composed of the nucleotide sequence represented by SEQ. ID. NO: 4 as an active ingredient.

The present invention further provides a method for treating inflammation containing the step of administering the said composition to a subject having inflammation.

The present invention also provides a method for preventing inflammation containing the step of administering the said composition to a subject.

The present invention also provides a diagnostic kit for inflammatory disease containing antibody or aptamer specifically binding to CD93 or soluble fragment of the same.

In addition, the present invention provides a diagnostic method for inflammatory disease using the said diagnostic kit for inflammatory disease.

Advantageous Effect

As explained hereinbefore, the present invention can provide an anti-inflammatory composition containing antibody specific to the soluble fragment of CD93 as an active ingredient, and the said composition can be effectively used for the prevention or treatment of inflammatory disease. The present invention can also provide a use of CD93 or its soluble fragment as a diagnostic marker for inflammatory disease, and this marker can be effectively used for diagnosis or monitoring of inflammatory disease.

BRIEF DESCRIPTION OF THE DRAWINGS

The application of the preferred embodiments of the present invention is best understood with reference to the accompanying drawings, wherein:

FIG. 1 is a set of diagrams showing the amino acid sequence of full length CD93 protein (FIG. 1A) and the amino acid sequence of sCD93 protein (FIG. 1B).

FIG. 2 is an electrophoresis photograph illustrating sCD93_Fc expressed in HEK293E cells and purified thereafter. Herein, N indicates non-reduced protein and R indicates reduced protein.

FIG. 3 is a set of photographs illustrating the adherence of THP-1 cells on the surface of dish.

FIG. 4 is a graph illustrating the adherence rate of THP-1 cells.

FIG. 5 is a set of photographs illustrating the differentiation of THP-1 cells into macrophages.

FIG. 6 is a set of graphs illustrating the expressions of macrophage differentiation markers.

FIG. 7 is a set of electrophoresis photographs illustrating the quantification of phospho-Erk 1/2, phospho-p38 and whole p38 by Western blotting.

FIG. 8 is a set of electrophoresis photographs illustrating the quantification of phospho-Erk 1/2 over the treatment time of sCD93 protein.

FIG. 9 is a set of graphs illustrating the expressions of TNF-α and IL-6 measured at RNA level after the treatment of sCD93 protein.

FIG. 10 is a set of graphs illustrating the expressions of IL-1β and iNOS measured at protein level after the treatment of sCD93 protein.

FIG. 11 is a set of graphs illustrating the expressions of IL-12, CXCL12, SPHK-1 and CLEC4A measured at protein level after the treatment of sCD93 protein.

DESCRIPTION OF THE PREFERRED EMBODIMENTS

Figure 3:
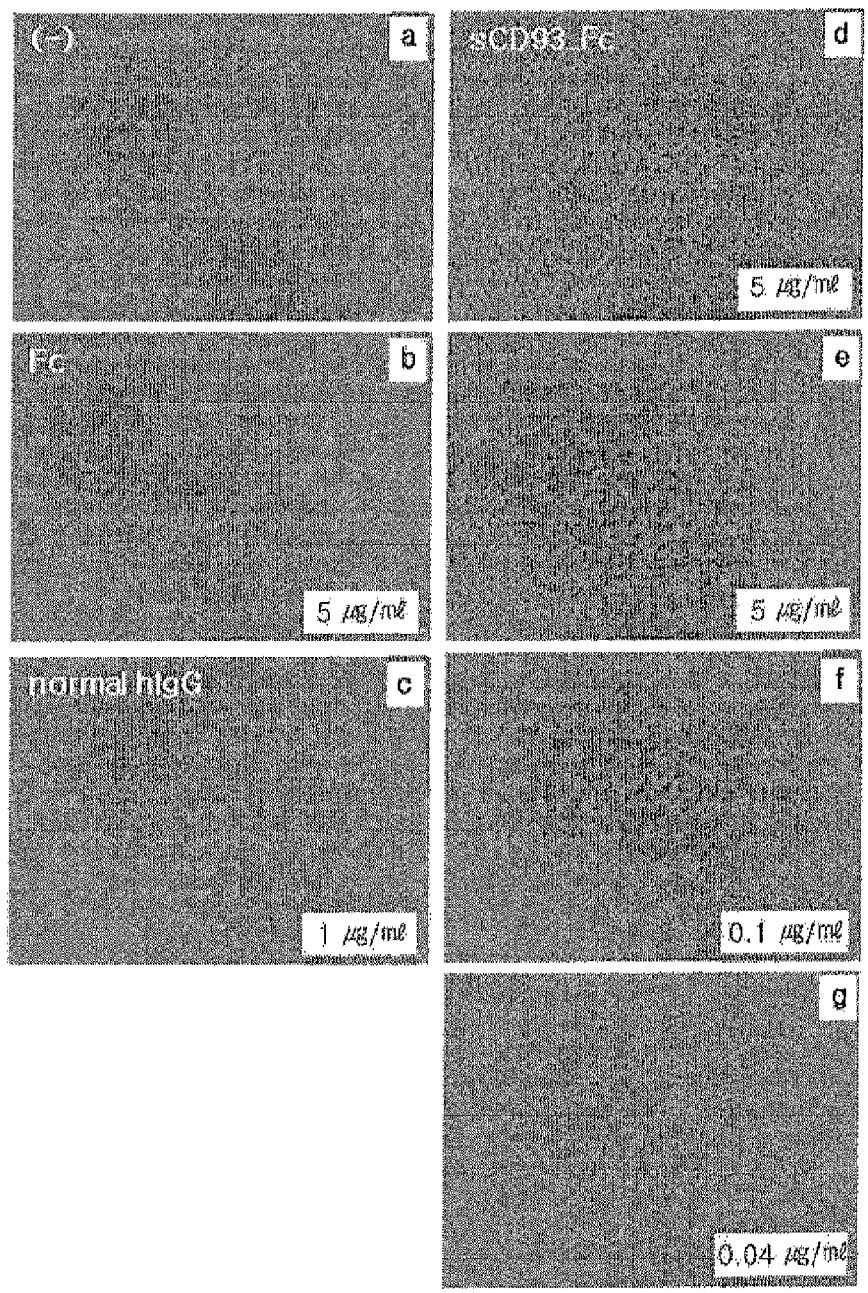
FIG. 3-FIG. 6 illustrate the differentiation of THP-1 cells into macrophages induced by sCD93.

Hereinafter, the present invention is described in detail.

The present invention provides an anti-inflammatory composition containing antibody specific to sCD93, the soluble fragment of CD93, as an active ingredient.

The present invention also provides a use of the antibody specific to sCD93, the soluble fragment of CD93, for the preparation of the anti-inflammatory composition.

The present inventors confirmed that THP-1 cells were differentiated into macrophages mediated by the activation of mitogen-activated protein kinase (MAPK), phagocytosis was induced, secretion of inflammatory cytokines such as TNF-α, IL-β, and IL-6 was increased, and secretion of matrix metalloproteinase (MMP) was accelerated, when THP-1 (human derived mononuclear cell line) was treated with sCD93.

The said MAPK is activated by inflammation inducing substances such as bacterial lipopolysaccarides, etc. Once it is activated, it accelerates the secretion of inflammatory cytokines. So, the secretion of MMP is accelerated in the process of inflammation response.

Considering such inflammation response inducing effect of sCD93, the present inventors studied and confirmed that the cytokine TNF-α known to be generated primarily by activated mononuclear cells or macrophages was decreased when THP-1 cells were treated with anti-sCD93 antibody.

The present invention has been built based on the result of the experiment proving the statement above. Therefore, the anti-inflammatory composition of the present invention characteristically contains sCD93 specific antibody as an active ingredient.

In this description, "sCD93" indicates the soluble fragment of CD93 which is fallen apart from the whole CD93, and the amino acid sequence and nucleotide sequence of the fragment are shown in <FIG. 1B> and represented by <SEQ. ID. NO: 1 and NO:2>. In this description, the target protein indicates sCD93, unless stated otherwise. The sequence of total length CD93 is shown in <FIG. 1A> and represented by <SEQ. ID.

NO: 3>. The nucleotide sequence of the gene of the protein is represented by <SEQ. ID. NO: 4>.

In this description, "anti-inflammatory" indicates prevention, improvement, treatment, and delay of inflammatory disease.

In this description, the said "inflammatory disease" indicates any state defined by local or systemic defense response against infection with foreign infectious agents such as physical or chemical stimuli, bacteria, fungi, virus, and various allergens, etc. This response accompanies a series of complicated physiological responses including activation of various inflammatory mediators and immune cell related enzymes (iNOS, COX-2, etc), secretion of inflammatory mediators (NO, TNF-α, IL-6, IL-β, and $PGE_2$), infiltration of body fluid, cell migration, tissue destruction, etc, and is shown as such symptoms as erythema, pain, edema, pyrexia, functional deficiency or loss, etc. The said inflammatory disease can be acute, chronic, ulcerative, allergenic, or necrotic, so if a disease is defined as inflammatory disease, it does not matter whether it is acute, chronic, ulcerative, allergenic, or necrotic. Particularly, the inflammatory disease herein is exemplified by asthma, allergic and non-allergic rhinitis, acute and chronic rhinitis, acute and chronic gastritis or enteritis, ulcerative gastritis, acute and chronic nephritis, acute and chronic hepatitis, chronic obstructive pulmonary disease, pulmonary fibrosis, irritable bowel syndrome, inflammatory pain, migraine, headache, lumbago, fibromyalgia, myofascial disease, viral infection (hepatitis C virus), bacterial infection, fungal infection, burn, wound by surgical or dental operation, hyper-prostaglandin E syndrome, atherosclerosis, gout, arthritis, rheumatoid arthritis, ankylosing spondylitis, Hodgkin's disease, pancreatitis, conjunctivitis, iritis, scleritis, uveitis, dermatitis, eczema, and multiple sclerosis, etc.

In this description, "an active ingredient" indicates an ingredient that is active by itself or with a pharmaceutically acceptable non-active carrier. The meaning of "pharmaceutically acceptable" is explained hereinafter.

In this description, "specific binding" indicates that antibody is conjugated with its target protein sCD93 to produce antigen-antibody complex but is not practically conjugated with any other proteins. Herein, "practically" means it can produce a non-specific conjugate with low chance, yet. Herein, "specific binding" can also be described as the binding that can be determined by antigenic determinant site, the specific protein structure called epitope.

In this description, "epitope" indicates the amino acid region (antigen determinant site) having antigenicity or immunogenicity in sCD93, the target protein. Epitope generally includes at least 10 amino acids. The epitope can be identified by the conventional method, such as phage display and reverse immunogenetics, which have been well-informed to those in the art.

In this description, "antibody" includes every kinds that can be specifically bind to sCD93, the target protein, which is exemplified not only by monoclonal antibody, polyclonal antibody, multispecific antibody (antibody that has specificity against at least two or more antigens or epitopes, ex, bispecific antibody), humanized antibody, human antibody, but also by antibody fragment, recombinant antibody, and chemically modified antibody that are able to bind specifically to sCD93, the target protein.

The humanized antibody indicates the antibody in which complementarity determining region (CDR) of human immunoglobulin is substituted with non-human CDR such as CDR of mouse, rabbit, rat, and apes, so as to minimize immunorejection. The preparation method of such antibody has been well-informed to those in the art. Details can be found in the following references (Riechmann L. et al., *Nature*, 332: 323-327, 1988; Nakatani T. et al., *Protein Engineering*, 7: 435-443, 1994; Jones et al., *Nature*, 321: 522-525, 1986; Presta, *Curr. Op. Struct. Biol.*, 2: 593-596, 1992).

The human antibody indicates the antibody obtained from an animal immunized with a specific antigen. In the animal such as mouse, the gene responsible for producing endogenous immunoglobulin has been destroyed and human immunoglobulin gene is inserted therein. Details can be found in the following references (Jakobovits et al., *Proc, Natl. Acad, Sci. USA*, 90: 2551, 1993; Jakobovits et al., *Nature*, 362: 255-258, 1993; Bruggermann et al., *Year in Immuno.*, 7: 33, 1993; Hoogenboom et al., *J. Mol. Biol.*, 227: 381, 1991; Marks et al., *J. Mol. Bio.*, 222: 581-597, 1991).

The antibody fragment herein is exemplified by Fab, F(ab'), F(ab')$_2$, scFv (antibody whose Fv of heavy chain or light chain is connected by a proper linker), Fv fragment, Fab/c (antibody having one Fab and complete Fc), linear antibody (Zapata et al., Protein Eng. 8(10):1057-1062 (1995)), antibody fragments obtained by treating antibody with protease such as papain and pepsin, and those antibody fragments obtained by genetic recombination technique characterized by introduction of gene corresponding to the fragment to host cells and expression therein. Globulin type of the said antibody is not limited as long as it can be specifically bound to the target protein sCD93, which can be selected from the group consisting of IgG, IgM, IgA, IgE, IgY, and IgD.

In the meantime, the polyclonal antibody can be prepared by immunizing such animal as birds (for example, fowl, etc), and mammals (for example, rabbit, goat, horse, sheep, rat, non-human apes like monkey, chimpanzee, and gorilla) with sCD93, the target protein. In general, antibody titer is measured by enzyme immunoassay (EIA and ELISA) or radio-immunoassay (RIA) after 6-60 days from the final immunization. When the antibody titer reaches the peak, blood work is performed. Antibody is purified from the blood sample by the conventional method such as ion exchange chromatography and affinity chromatography, etc.

The monoclonal antibody can be obtained from the hybridoma cell line producing sCD93 specific monoclonal antibody. To generate such hybridoma cell line, an animal (for example, mouse) is immunized with the target protein sCD93, and then spleen cells are extracted from the immunized animal. The spleen cells are fused with myeloma cells, leading to the production of hybridoma cells. Finally, the hybridoma cell line producing monoclonal antibody is identified. Isolation or recovery of monoclonal antibody from the hybridoma cell line can be performed by the conventional method well-informed to those in the art.

The preparation of the monoclonal antibody is described in detail hereinafter.

First, to obtain the monoclonal antibody, the target protein sCD93 is administered to mammals, for example, rat, mouse, rabbit, monkey, goat, and non human apes (monkey, chimpanzee, and gorilla), etc. One time dose of immunogen is determined by those in the art with considering the kind of test animal, administration pathway, etc, which should be appropriate and generally acceptable. In general, one-time dose can be 50-200 μg per animal. For the administration, immunogen is diluted with or suspended in PBS (phosphate-buffered saline) or saline, which is then mixed with a proper adjuvant. After emulsification, it is administered hypodermically or intraperitoneally. Administration is preferably performed 2-10 times at a few days or a few weeks intervals, more preferably 1-4 weeks intervals, and most preferably 3-4 times at that intervals. During the administration, antibody titer of the immunized animal serum is measured by ELISA. When the antibody titer reaches plateau, the immunogen is administered intravenously or intraperitoneally one last time. After 2-5 days from the final administration, antibody producing cells are collected. The antibody producing cells can be exemplified by spleen cells, lymph node cells, peripheral blood cells, etc, but spleen cells or lymph node cells are preferred.

After collecting antibody producing cells, hybridoma cell line producing the monoclonal antibody specific to the target protein sCD93, the immunogen introduced therein, is constructed. Such hybridoma cell line can be produced and identified by the conventional method well-informed to those in the art. In general, antibody producing cells, preferably spleen cells are extracted from the immunized animal, and then the extracted spleen cells are fused with myeloma cells to construct hybridoma cells, followed by identification of the hybridoma cell line producing monoclonal antibody specifically binding to the immunogen. As the myeloma cell line used for fusion with the antibody producing cells, the cell line originated from an animal such as a mouse can be used. Such cell line can also be purchased. The preferable myeloma cell line is the one originated from the animal which is the same line of the immunized animal, has drug selectivity to antibiotics, etc, and cannot survive in HAT selection medium containing hypoxanthine, aminopterine, and thymine without being fused with spleen cells, but only can survive as being fused with spleen cells. The myeloma cell line is exemplified by P3X63 (ATCC TIB9), the HGPRT⁻ (hypoxanthine guanine phosporibosyl-transferase negative) cell line originated from BALB/c mouse.

The fusion of antibody producing spleen cells with myeloma cell line is performed in serum-free DMEM or RPMI-1640 at a proper ratio (1:1-20:1) in the presence of cell fusion accelerator. As the cell fusion accelerator, poly ethylene glycol (average molecular weight: 1500-4000) can be used at the concentration of 10-80%. To increase fusion efficiency in some cases, such adjuvant as dimethylsulfoxide can be added. Or commercial cell fusion device can also be used for the fusion.

After cell fusion, target hybridoma is selected. In general, cell suspension is properly diluted with RPMI-1640 supplemented with FBS, followed by distribution on micro-titer plate at the density of 20,000 cells per well. Selection medium is added to each well and the medium is replaced with the same selection medium properly to provide fresh medium for culture. Preferable culture temperature is 20-40° C. When the myeloma cell line is HGPRT deficient or thymidine kinase deficient cell line, the selection medium containing hypoxantine, aminopterine and thymidine (HAT medium) is used to culture and proliferate hybridoma cells of antibody producing cells and myeloma cell line selectively. Approximately around 14 days from beginning of the culture in such selection medium, hybridoma cells can be obtained. Target antibody is screened with the supernatant of the growing hybridoma culture solution. The screening can be performed by the conventional method well-known to those in the art. For example, enzyme immunoassay (EIA and ELISA) and radioimmunoassay, etc can be used. Cloning of fused cell can be performed by limiting dilution method.

The cloned hybridoma is cultured in animal cell culture medium such as RPMI-1640 containing 10% FBS, DMEM, or serum-free medium under the conventional culture condition (For example, 37° C., 5% $CO_2$). Duration of culture is preferably 2-10 days. Monoclonal antibody can be obtained from the supernatant of the culture solution.

Collection of monoclonal antibody can be performed by the conventional method well-known to those in the art, which is selected from the group consisting of ammonium sulfate fractionation, ion exchange chromatography, affinity chromatography, gel filtration chromatography, and combinations of those.

For the production of the monoclonal antibody of the present invention, genetic recombination technique, that is the process comprising cloning antibody gene from hybridoma; introducing the gene into a proper vector; transfecting host cells with the vector; and expressing the gene, can be used (Vandamme, A. M. et al., Eur. J. Biochem., 192, 767-775, 1990).

Particularly, mRNA encoding variable region (V region) of the antibody of the present invention is obtained from the hybridoma producing the antibody of the invention. Total RNA is obtained by the conventional method well-informed to those in the art such as guanidine ultracentrifugation (Chirgwin, J. M. et al., Biochemistry., Vol 18, 5294-5299, 1979) and AGPC (Chomczynski, P. et al., Anal. Biochem., 162, 156-159), etc. Then, target mRNA is obtained from the total RNA by using mRNA purification kit (Pharmacia). As an alternative, QuickPrep mRNA purification kit (Pharmacia) can also be used to obtain mRNA directly.

From the obtained mRNA, cDNA of variable region of the antibody is synthesized by using reverse transcriptase. If necessary, RACE PCR can be used for cDNA synthesis or amplification. The synthesized cDNA encoding variable region is introduced into an expression vector comprising DNA encoding constant region (C region). This expression vector can contain regulatory sequence such as promoter, enhancer, replication origin, polyadenylation signal, and ribosome binding site, etc. Once host cells are transformed with this expression vector, they can produce antibody. For the expression of antibody gene, DNA encoding antibody heavy chain (H chain) or light chain (L chain) is inserted in the expression vector respectively to transform host cells. Or it is still possible to introduce DNA encoding heavy chain and light chain in the expression vector to transform host cells (WO 94/11523).

The immunogen used for the production of antibody of the present invention, that is the target protein of the invention sCD93, can be prepared by the conventional genetic recombination technique well-known to those in the art. In general, cDNA of the target protein sCD93 is constructed, which is then inserted in an expression vector. Prokaryotic or eukaryotic host cells are transformed with the expression vector, which are then cultured in proper medium. Then, the target protein is obtained from the culture solution or cultured cells. The said cDNA can be constructed by the conventional method based on gene sequences provided by gene/protein database such as GenBank, etc or sequences provided by this description.

For the construction of cDNA, DNA synthesizer using phosphoramidite, RT-PCR, or hybridization using cDNA library can be used. If necessary, target cDNA can be amplified by PCR.

The expression vector herein can be purchased from one of biotech companies such as Novagen, Dakara Shuzo, Qiagen, Stratagene, Promega, Roche Diagnositics, Invitrogen, and Genetics Institute, etc.

Such expression vector can include control elements such as promoter, enhancer, polyadenylation signal, ribosome binding site, replication origin, terminator, selection marker, and marker peptide sequence for deletion or purification (for example, nucleotide sequence encoding histidine repeats), in addition to DNA encoding the target protein sCD93.

As the host cells, prokaryotic cells including bacteria (for example, *E. coli* and *Bacillus subtilis*) and eukaryotic cells including yeast (for example, *Saccharomyces cerevisiae*), insect cells (for example, sf cells), mammalian cells (for example, COS, CHO, BHK), etc can be used.

For the purification of the target protein of the present invention from host cells or culture solution thereof, ultrafiltration, gel filtration, ion exchange chromatography, affinity chromatography (if marker peptide is conjugated), HPLC, hydrophobic chromatography, isoelectric chromatography, or their combinations can be used.

Production of the target protein of the present invention based on DNA recombination technique is referred to the following references (Sambrook et al, Molecular Cloning A Laboratory Manual, Cold Spring Harbor Laboratory Press, US(1989); Ausubel et al, Current Protocols in Molecular Biology, Jon Willey & Sons, US(1993); and Sambrook, J. & Russel, D., Molecular Cloning, A LABORATORY MANUAL, Cold Spring Harbor Laboratory Press, 1:7.42-7.45, 2:8.9-8.17, 2001). Those references are considered as a part of this description.

As the immunogen used for the production of antibody of the present invention, sCD93 fragment or total length CD93 can be used because antibody obtained by using either fragment or full-length protein is capable of being bound specifically to the target protein of the present invention.

The present invention also provides an anti-inflammatory composition containing one or more substances selected from the group consisting of siRNA, shRNA, and shRNA expression vectors capable of suppressing the expression of CD93 gene composed of the nucleotide sequence represented by SEQ. ID. NO: 4 as an active ingredient.

The present invention further provides a use of one or more substances selected from the group consisting of siRNA, shRNA, and shRNA expression vectors capable of suppressing the expression of CD93 gene for the production of an anti-inflammatory composition.

The present inventors confirmed that inflammatory cytokines such as TNF-α and IL-6 which are increased usually by the treatment of LPS (lipopolysaccharide) were down-regulated when siRNA against CD93 gene was treated to THP-1.

When siRNA (small interfering RNA) or shRNA (short hairpin RNA) which are gene specific short double stranded RNAs are introduced in cells, they are processed by ribonuclease dicer to be bound to RISC (RNA induced gene silencing complex) to induce RNAi (Nature 391, 806-811, 1998; Genes Dev. 15, 485-490, 2001; Nature 411, 494-498, 2001; Science 287, 2494-2497, 2000; Cell 101, 25-33, 2000). Helicase and endonuclease are involved in RNAi. Particularly, double stranded RNA of siRNA is untied by helicase. Antisense strand of them is bound to mRNA of target gene and the binding site is hydrolyzed by endonuclease (Cell 101, 25-33, 2000; Science 296, 1265-1269, 2002; J. Biol. Chem. 2003 Feb. 28: 278(9):7108-18).

In this description, "siRNA" indicates double stranded RNA comprising 10-40 base pairs, more preferably 15-30 base pairs, and most preferably 20-22 base pairs capable of inducing RNAi phenomenon against target gene RNA. This siRNA has either blunt end or overhang. When it has overhang, it can be both on 3' and 5'ends, but 3'end is preferred. The number of nucleotides on overhang is 1-5, and more preferably 2-3.

In this description, "shRNA" indicates hairpin structured double stranded RNA having loop region comprising 2-10 nucleotides. Nucleotides of the loop region can be selected as ones well-known to those in the art (Proc. Natl. Acad. Sci. US A 99(8): 5515-5520, 2002; Nature Biotechnology 20: 505-508, 2002; Nature Biotechnology 20 : 500-505, 2002; Nat Cell Biol. 5:489-490, 2003; Proc. Natl. Acad. Sci. USA 99(9): 6047-6052, 2002). Constitution of double stranded region of the shRNA is same as that of the siRNA, and thus no further explanations are required.

In this description, "shRNA expression vector" indicates the vector able to express shRNA in host cells by containing shRNA coding sequence therein. The said shRNA coding sequence is composed of a part of CD93 gene, spacer sequence composing loop region, and complementary sequence to the part of CD93 gene. The shRNA coding sequence can be either RNA or DNA, depending on the expression vector to be used, and is operatively linked to regulatory sequence of the expression vector (for example, promoter, polyadenylation signal, etc). The expression vector can be plasmid vector or lentivirus vector. The plasmid vector can be purchased from one of biotech companies such as Promega (Cat. Nos. C8750, C8760, C8770, C8780, C8790, C7800, etc) and Genscript (Cat. Nos. SD1201, SD1202, SD1207, etc), or can be constructed. The use of lentivirus vector is described in W02004/06549.

The composition of the present invention can include pharmaceutically acceptable carriers in addition to anti-sCD93 antibody, siRNA, and shRNA. Herein, "pharmaceutically acceptable" indicates that the composition has no more toxicity than applicable to a treatment subject (low and safe enough toxicity) without limiting activity of the active ingredient. Such carrier is exemplified by water, saline, dextrose, glycerol, ethanol, polyalcohol (for example, mannitol, sorbitol, etc), and sodium chloride, etc.

The composition of the present invention can also include preservatives, anti-oxidants, wetting agents, emulsifying agents, buffers, and non-ionic surfactants to extend shelf-life or to reserve effectiveness. Proper examples of those preservatives, anti-oxidants, and wetting agents are well-informed to those in the art.

The composition of the present invention can be formulated in a variety of forms, for example, solution, suspension, syrup, tablet, pill, etc, but not always limited thereto.

The composition of the present invention can be administered orally or parenterally to mammals including human. In general, like any other bio medicines including antibody as an active ingredient, the composition of the present invention can be administered by intravenous injection, hypodermic injection, intraperitoneal injection, and intramuscular injection, but not always limited thereto.

The effective dose of the composition of the present invention can be determined by an expert in the field of medicine considering effectiveness, severity of disease, patient weight, drug formulation, administration pathway and duration, etc, but generally it is determined in the range of 0.01 µg/kg/day-100 mg/kg/day, but not always limited thereto.

The present invention also provides a diagnostic marker for inflammatory disease comprising CD93 or its soluble fragment as an active ingredient.

The said CD93 has preferably the amino acid sequence represented by SEQ. ID. NO: 33, but not always limited thereto.

The soluble fragment of CD93 is preferably the 95 kDa ectodomain of CD93, the transmembrane protein, released after cell culture, but not always limited thereto.

The expression of CD93 in this invention was increased in the human mononuclear cell line THP-1 not by the treatment of PMA but by the treatment of LPS and TNF-α. However, the amount of CD93 soluble fragment was increased by the treatment of LPS, TNF-α, and PMA as well. After injecting PBS, thioglycollate, and LPS to a mouse, CD93 expression in mouse macrophages was confirmed to increase mostly by LPS treatment and the treatment of thioglycollate brought a similar result. The amount of CD93 soluble fragment in serum was not changed much by the treatment of LPS or thioglycollate. However, the amount of CD93 soluble fragment in peritoneal lavage fluid was significantly increased by the treatment of LPS or thioglycollate.

In the meantime, CD93 expression was significantly high in synovial membrane tissue obtained from rheumatoid arthritis patient, compared with in synovial membrane tissue obtained from osteo-arthritis patient. Consistently, the amount of CD93 soluble fragment was significantly high in synovial fluid obtained from rheumatoid arthritis patient, compared with in that in synovial fluid obtained from osteo-arthritis patient.

As explained hereinbefore, the CD93 or its soluble fragment of the present invention is up-regulated under inflammatory environment, that is in the presence of inflammation inducing substances. Therefore, the CD93 or its soluble fragment of the present invention can be effectively used as a diagnostic marker for inflammatory disease.

The inflammatory disease herein is exemplified by asthma, allergic and non-allergic rhinitis, acute and chronic rhinitis, acute and chronic gastritis or enteritis, ulcerative gastritis, acute and chronic nephritis, acute and chronic hepatitis, chronic obstructive pulmonary disease, pulmonary fibrosis, irritable bowel syndrome, inflammatory pain, migraine, headache, lumbago, fibromyalgia, myofascial disease, viral infection, bacterial infection, fungal infection, burn, wound by surgical or dental operation, hyper-prostaglandin E syndrome, atherosclerosis, gout, arthritis, rheumatoid arthritis, ankylosing spondylitis, Hodgkin's disease, pancreatitis, conjunctivitis, iritis, scleritis, uveitis, dermatitis, eczema, and multiple sclerosis, etc, but not always limited thereto.

The present invention also provides a diagnostic kit for inflammatory disease containing antibody or aptamer specifically binding to CD93 or soluble fragment of the same.

The present invention also provides a use of antibody or aptamer specifically binding to CD93 or its soluble fragment for the preparation of the diagnostic kit for inflammatory disease.

The diagnostic kit for inflammatory disease herein can be easily prepared by the conventional method well-known to those in the art using the CD93 or its soluble fragment marker of the present invention. The said aptamer is single stranded nucleic acid (DNA, RNA or modified nucleic acid) characterized by the stable tertiary structure, high affinity to target molecule, and specificity to target.

The diagnostic kit for inflammatory disease herein can include antibody specifically binding to CD93 or its soluble fragment, secondary antibody conjugate conjugated with a marker colored by reaction with substrate, chromogenic substrate solution to respond with the marker, washing solution, and enzyme reaction terminating solution, etc.

The present invention also provides a diagnostic method for inflammatory disease using the CD93 or its soluble fragment marker of the present invention.

Particularly, the said method is preferably performed by the following steps, but not always limited thereto:

1) coating biological sample and control protein on a fixture;

2) inducing antigen-antibody reaction by adding the antibody specifically binding to CD93 or its soluble fragment, the diagnostic marker for inflammatory disease, to the above fixture;

3) detecting the antigen-antibody reaction product produced by the above antigen-antibody reaction by using a secondary antibody conjugate marker and chromogenic substrate solution; and 4) comparing the detection results between the biological sample and the control.

The biological sample herein is preferably one or more materials selected from the group consisting of tissue, cell, blood, serum, peritoneal lavage fluid, synovial fluid, saliva, urine, and feces, but not always limited thereto.

In the above method, the secondary antibody conjugate marker is preferably the conventional coloring agent appropriate for color development, which is exemplified by such fluoresceins as HRP (horseradish peroxidase), alkaline phosphatase, colloid gold, FITC (poly L-lysine-fluorescein isothiocyanate), RITC (rhodamine-B-isothiocyanate, and dye, etc.

In this method, the chromogenic substrate solution can be used according to the marker, which is exemplified by TMB (3,3',5,5'-tetramethyl bezidine), ABTS [2,2'-azino-bis(3-ethylbenzothiazoline-6-sulfonic acid)], and OPD (o-phenylenediamine), etc. At this time, the chromogenic substrate is preferably provided as dissolved in buffer (0.1M NaOAc, pH 5.5).

The washing solution herein preferably includes phosphate buffer, NaCl, and Tween 20, and is more preferably the buffer (PBST) composed of 0.02 M phosphate buffer, 0.13 M NaCl, and 0.05% tween 20. This washing solution is added to the fixture after the reaction of secondary antibody with the antigen-antibody conjugate, followed by washing 3-6 times, but not always limited thereto. As the reaction terminating solution, sulfuric acid solution can be used.

According to the present invention, early diagnosis or prognosis of inflammatory disease can be possible by detecting CD93 or its soluble fragment by antigen-antibody reaction using the antibody specifically binding to CD93 or its soluble fragment in biological sample. The biological sample herein is selected from the group consisting of tissue, cell, blood, serum, peritoneal lavage fluid, synovial fluid, saliva, urine, and feces, but not always limited thereto. Particularly, CD93 or its soluble fragment included in a biological sample is fragmented by SDS-PAGE, and the resultant fragment is transferred onto the fixture. The antibody specifically binding to the fixed CD93 or its soluble fragment is added to induce antigen/antibody reaction. Then, the expression of CD93 or its soluble fragment is measured. If the expression of CD93 or its soluble fragment in the biological sample is high, it can be diagnosed as inflammatory disease or high risk of getting inflammatory disease.

In this method, the fixture used for antigen-antibody reaction can be nitrocellulose membrane, PVDF membrane (polyvinylidene difluoride membrane), 96-well plate made of polyvinyl resin or polystylene resin, and glass slide glass, etc.

In this method, the antigen/antibody reaction can be measured by the conventional ELISA, radioimmunoassay (RIA), sandwich ELISA, Northern blotting, Western blotting, immunoprecipitation, immunohistochemical staining, immunofluorescence method, enzyme-substrate colorimetric method, antigen-antibody agglutination, SPR (surface plasmon resonance), biochip (DNA, RNA), electrophoresis, PCR, and RT-PCR, etc.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Preparation of sCD93 Protein

<1-1> Construction of pYW600
<1-1-1> Insertion of oriP

First, to clone oriP, PCR was performed using pMEP4 (Invitrogen, USA) as a template with a forward primer (5'-gt agatctgcaggaaaaggacaagc-3'; SEQ. ID. NO: 27) and a reverse primer (5'-cgagatctggttgacttccctaatgt-3'; SEQ. ID. NO: 28) with the cycle of 95r for 30 seconds, 60° C. for 30 seconds, and 72° C. for 1 minute (30 cycles). Then, 2187 by PCR product was purified by using PCR purification kit (Promega, USA). Next, the PCR product was digested with BglII (Invitrogen, USA), and the fragment was purified. The purified fragment was inserted into the BglII recognition site located upstream of CMV promoter of pcDNA3.1 (Invitrogen, USA) linearized by BglII (Invitrogen, USA). Transformant (pcDNA3.1-oriP) was obtained by transfecting *E. coli* with the vector. From the transformant, plasmid was extracted by the conventional method. Then, the insertion of oriP was confirmed by nucleotide sequencing.

<1-1-2> Insertion of Polynucleotide Encoding Human Antibody Fc

To insert polynucleotide encoding human antibody Fc into pcDNA3.1 vector in which oriP was introduced, PCR was performed using pLCN-MoH vector (Korean Patent No. 450266) as a template with a forward primer (5'-cgg gat cc g gcc gtg ggg gcc gac aaa a ct cac aca tgc c-3'; SEQ. ID. NO: 29) composed of 'Bam HI-SfiI-human immunoglobulin Fc N-terminal sequence' and a reverse primer (5'-cgagtc tca ttt acc cgg aga cag gga-3'; SEQ. ID. NO: 30) composed of 'XbaI-stop codon-human immunoglobulin Fc C-terminal sequence' as follows: 94° C. for 4 minutes; 95° C. for 30 seconds, 60° C. for 30 seconds, 72° C. for 1 minute, 30 cycles; and final extension at 72° C. for 10 minutes.

Then, the PCR product was purified by using PCR purification kit (Promega, USA). The fragment was inserted in pcDNA3.1-oriP vector predigested with BamHI and XbaI, resulting in the construction of pcDNA3.1-oriP-Fc. *E. coli* (DH5a) was transfected with the constructed recombinant plasmid. Then, the resultant transformant was isolated. Plasmid was extracted and investigated to confirm whether or not the polynucleotide encoding Fc was correctly inserted. As a result, pYW600 was constructed.

<1-1-3> Expression and Purification of sCD93-Fc

To express/purify sCD93_Fc in the animal cell line HEK293E, an expression vector capable of expressing sCD93_Fc was constructed.

The constructed pYW600 containing human IgG1 Fc fragment was digested with SfiI, to which CD93 fragment obtained by PCR and digested with SfiI was inserted. To amplify CD93 fragment, PCR was performed using CD93 plasmid (Kugi, hMU003993, Kugi No. IRAT-49-A06) as a template with a forward primer (5'-CAGGGGGC-CGTGGGGGCCACGGGAGCTGACACGGAGGC-3'; SEQ. ID. NO: 31) and a reverse primer (5'-TAGCGGC-CGACGCGGCCAAGTCCACACAGTCCAGCTGAC-3'; SEQ. ID. NO: 32). For the PCR, 100 ng of the template, 10 µmol of each primer, and 0.5 ul of Pfu DNA polymerase (2.5 unit/ul) were used. Total volume of the reaction mixture was 50 ul. The conditions for CD93 PCR were as follows: predenaturation at 94° C. for 2 minutes, denaturation at 94° C. for 30 seconds, annealing at 55° C. for 30 seconds, polymerization at 72° C. for 1 minute, 30 cycles from denaturation to polymerization, and final extension at 72° C. for 10 minutes. The PCR product was digested with SfiI, which was inserted in pYK 602 vector wherein CMV I.E enhancer/promoter, leader sequence, CD93 gene, 6×His tag, Fc, Myc, and 8×His tag were sequentially located. As a result, pYK-CD93_Fc vector was constructed.

20 µg of the pCD93_Fc constructed above was mixed with 40 µg of polyethylenimine (PEI, Polysciences), which was introduced in HEK293E cells grown in 150 mm dish in advance. The culture medium was collected every other day for 8 days, followed by filtering. The filtrate was purified using protein A sepharose (Amersham). The purified sample was quantified by PEIRCE (Coomassie protein assay reagent), and the size was investigated on SDS-PAGE gel (FIG. 2). As reduced (R), sCD93_Fc was 70 kDA and as non-reduced (N) it was 140~150 kDa.

Example 2

Induction of Differentiation of THP-1 Cells into Macrophages by sCD93 Protein THP-1 cells, the human originated acute monocytic leukemia cells, are eventually differentiated into macrophages via adherence, spreading, and maturation by chemical substances such as PMA, etc. In this experiment, induction of THP-1 cell differentiation into macrophages by sCD93 was investigated.

Figure 4:
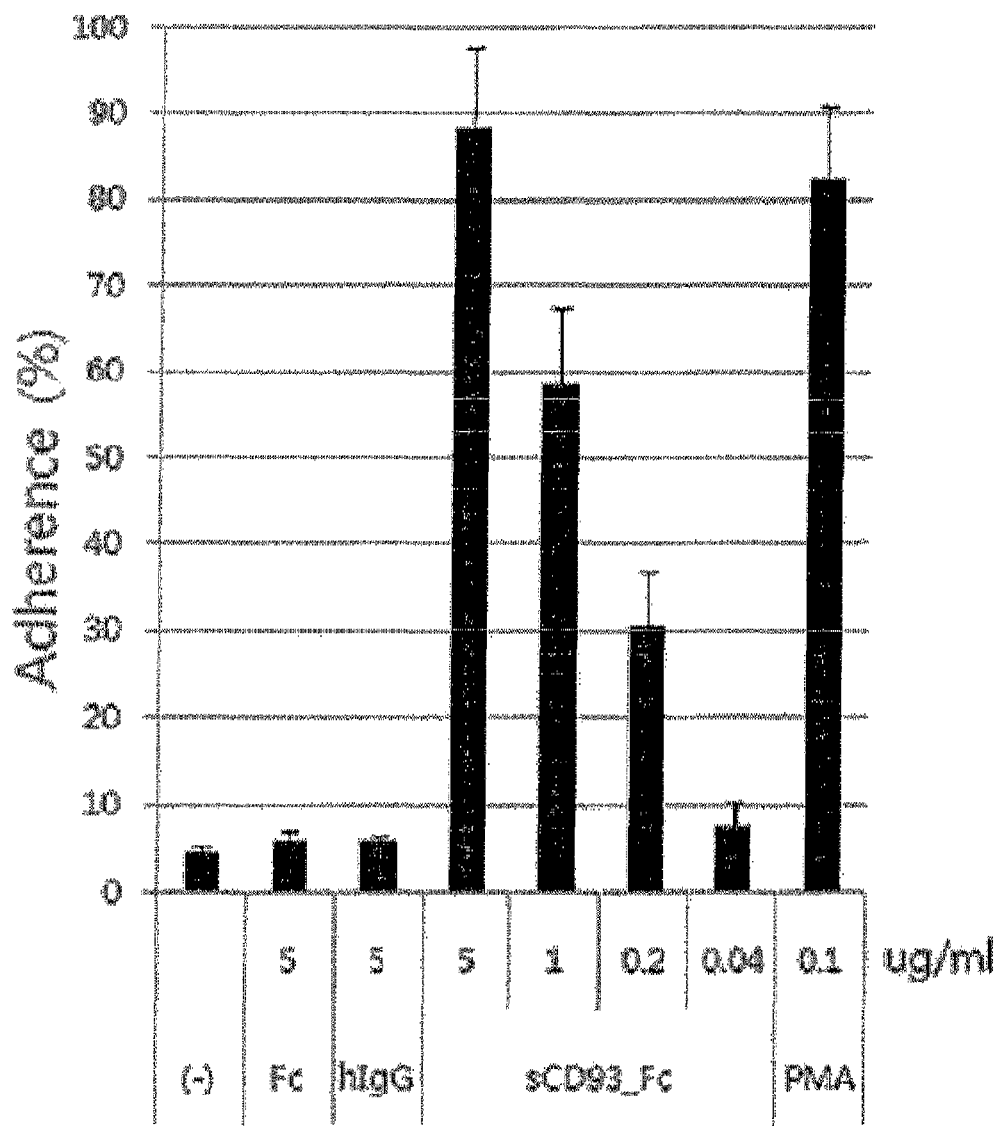

First, $5 \times 10^3$ THP-1 cells (purchased from ATCC) were distributed in 96-well plate. Negative control THP-1 cells were treated with PBS, Fc (5 µg/ml), and normal human IgG (hIgG, 5 µg/ml). Positive control THP-1 cells were treated with PMA (Sigma, 0.1 µg/ml). Experimental group THP-1 cells were treated with sCD93_Fc at the different concentrations of 5, 1, 0.2, and 0.04 µg/ml. After the treatment, they stayed in 37° C. incubator for 30 minutes. Then, all the groups were taken out to eliminate non-attached cells with tapping carefully not to lose any attached cells. After washing twice with PBS, photographs were taken under optical microscope (Leika) (FIG. 3). Non-attached cells in the culture supernatant were counted using hematocytometer (Marienfeld, Germany). Non-attached cell number was subtracted from the original cell number and the produced number was presented as %. THP-1 cells were not attached in the negative control, but highly attached in the experimental group treated with sCD93_Fc dose-dependently (presented by %) (FIG. 4).

Figure 5:
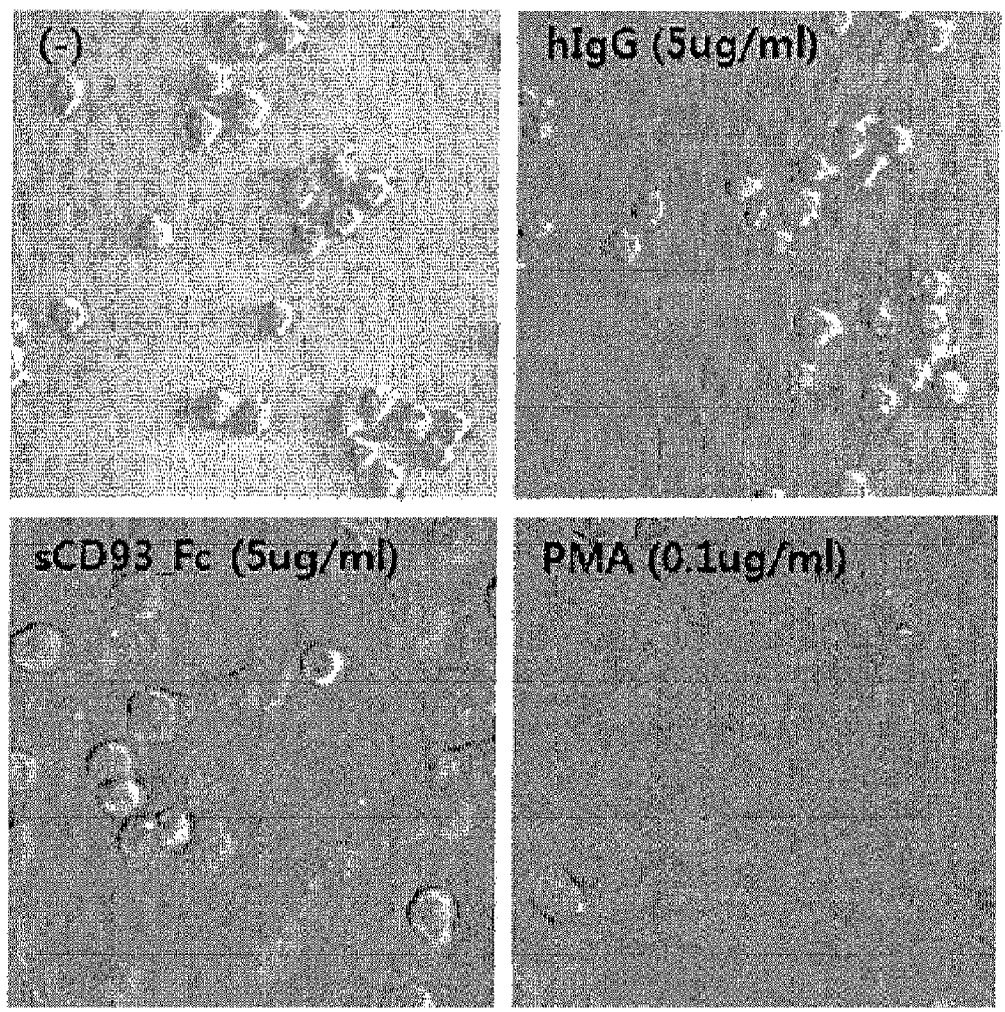

Next, effect of sCD93_Fc on THP-1 cell differentiation was investigated by the same manner as described hereinbefore. Particularly, negative control THP-1 cells were treated with PBS(−) and 5 µg/ml of hIgG. Positive control THP-1 cells were treated with 0.1 µg/ml of PMA. Experimental group THP-1 cells were treated with 5 µg/ml of sCD93_Fc. Each group was cultured for three days, followed by taking pictures under optical microscope. Differentiation was not induced in the negative control. THP-1 cells treated with sCD93_Fc were differentiated to macrophage-like cells similarly to the cells treated with PMA (FIG. 5).

To investigate whether THP-1 cells, the human mononuclear cells, were actually differentiated to macrophages, real-time PCR was performed to measure RNA expressions of CD14, CD1a and CD64, the markers of macrophages, dendrites, and neutrophils. Negative control THP-1 cells were treated with PBS(−) and 5 µg/ml of hIgG, and positive control THP-1 cells were treated with 0.1 µg/ml of PMA. Experimental group THP-cells were treated with 5 µg/ml of sCD93_Fc. 24 hours later, LPS was treated thereto to investigate susceptibility. 24 hours after the treatment, RNA was extracted and purified (Qiagen RNA miniprep kit). 1 µg of the purified RNA proceeded to reverse transcription (iScript cDNA synthesis kit, Bio-Rad) to synthesize cDNA. Quantitative-PCR was performed using the synthesized cDNA, the primers shown in Table 1, and iG SYBR Green supermix (Bio-Rad) with CFX-96 Real-time system (Bio-Rad).

Figure 6:
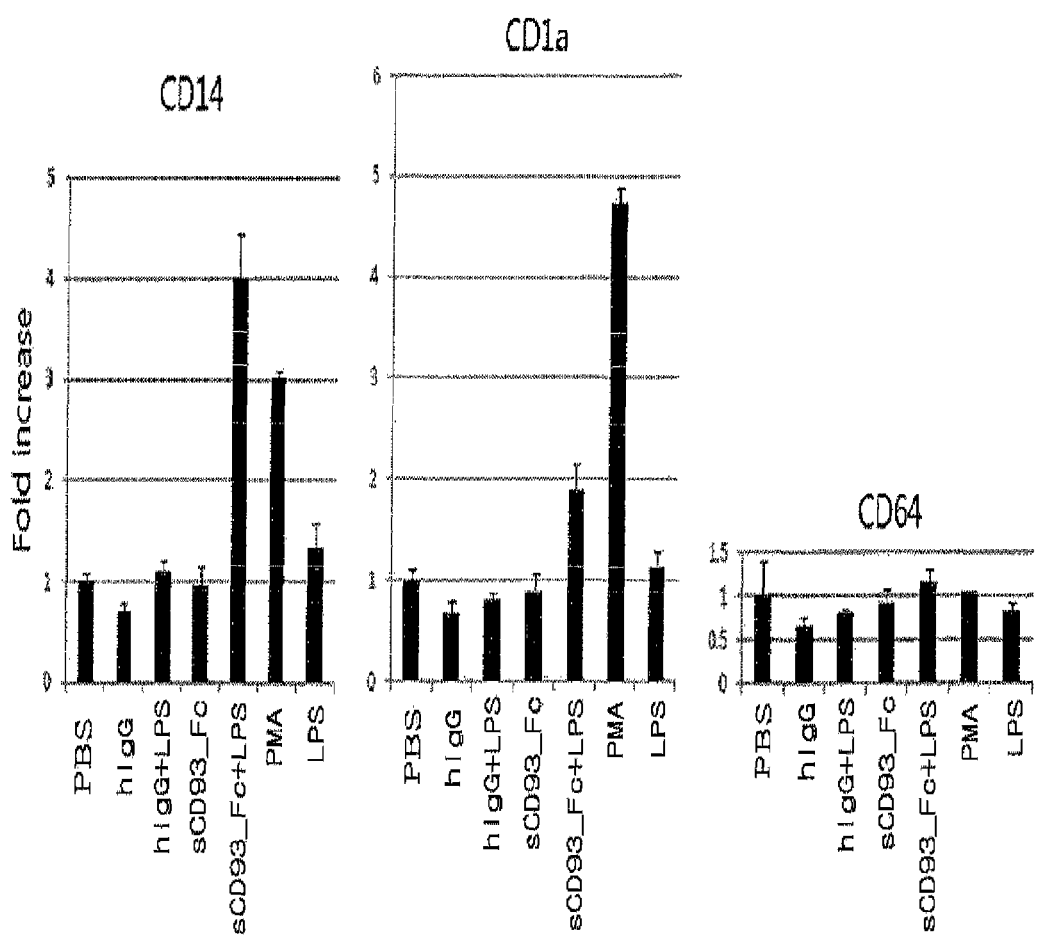

As a result, it was confirmed that THP-1 cells could be differentiated to macrophages by the treatment of sCD93. In the meantime, LPS treatment triggered the increase of CD14 RNA, the differentiation marker (FIG. 6).

Quantitative-PCR was performed using the synthesized cDNA, the primers shown in Table 2, and iG SYBR Green supermix (Bio-Rad) with CFX-96 Real-time system (Bio-Rad).

Figure 9:
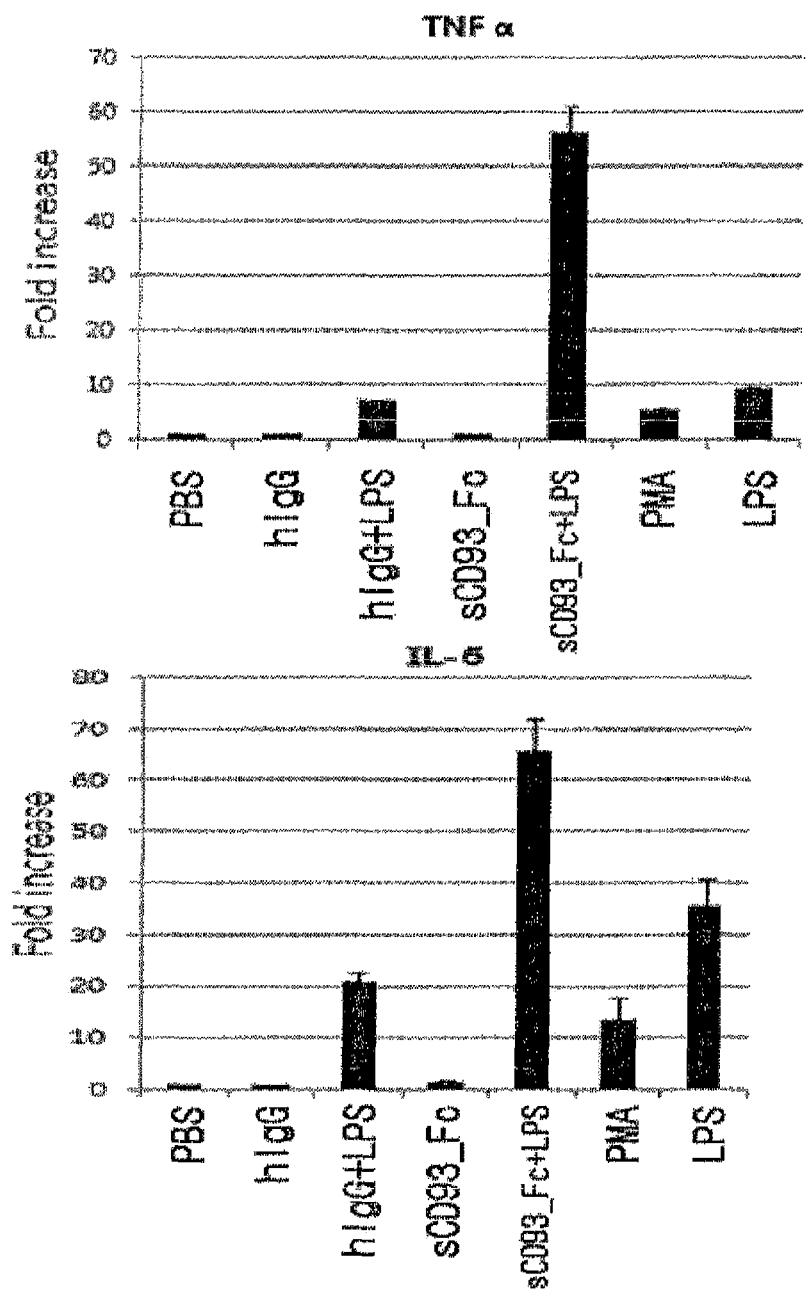
Figure 10:
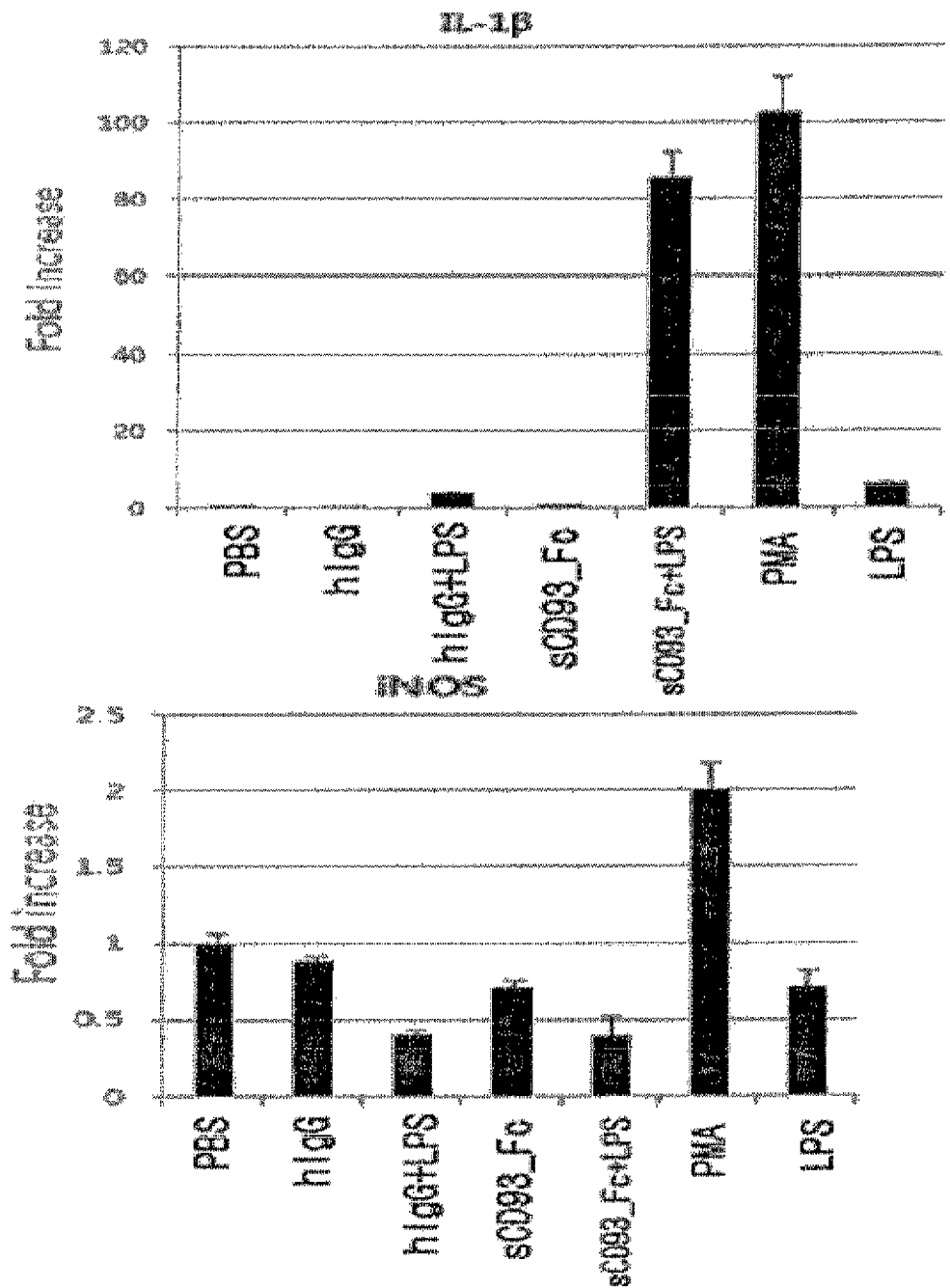
Figure 11:
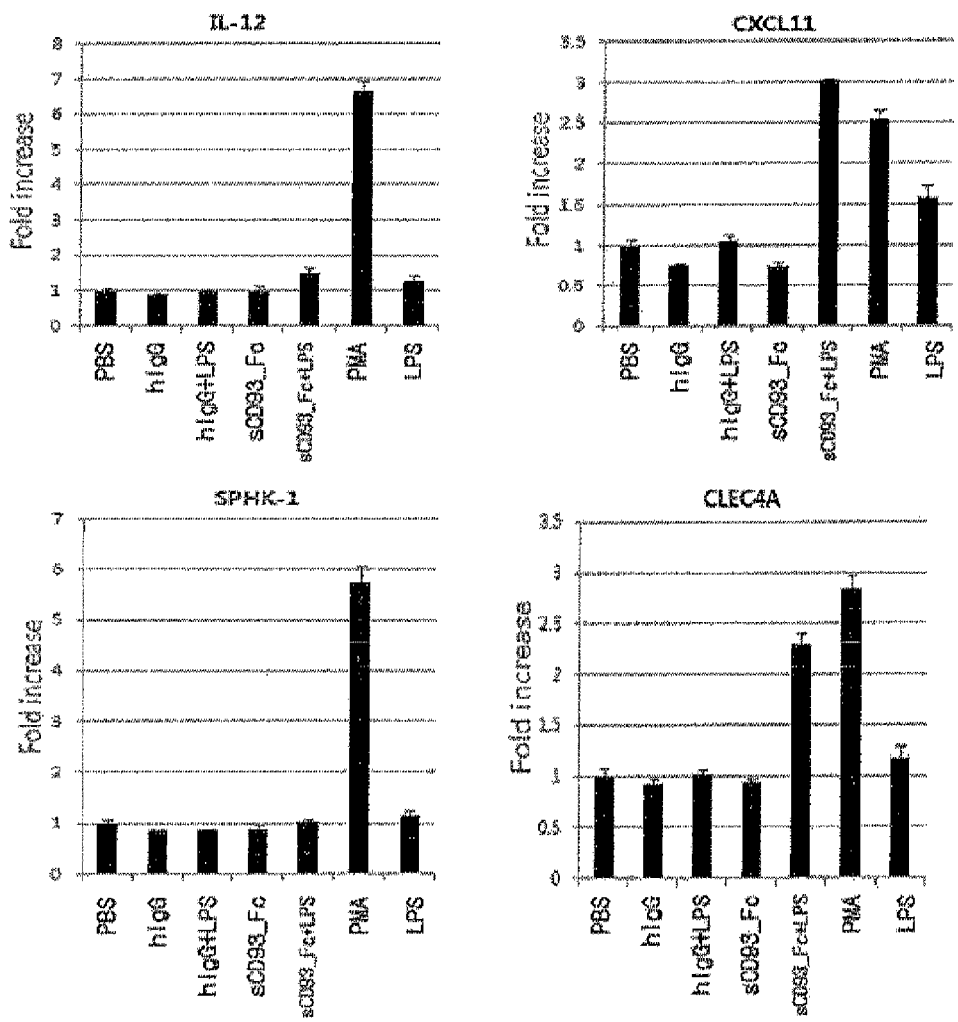

As a result, sCD93_Fc treatment caused the increase of pro-inflammatory cytokines TNF-α, IL-1b, and IL-6 at RNA level and this increase was more significant when LPS was additionally treated thereto (FIGS. 9-11).

TABLE 1

Primer sequence

| Differentiation Marker | Forward | Reverse |
|---|---|---|
| CD14-New | GCCTAGACCTCAGCCACAACTC (SEQ. ID. NO: 5) | CCAGCCCAGCGAACGACAG (SEQ. ID. NO: 6) |
| CD64-New | GGGTCAGCGTGTTCCAAGAGG (SEQ. ID. NO: 7) | GCACCTGTATTCACCACTGTCATTG (SEQ. ID. NO: 8) |
| CD1a-New | ACT CAT ACC TGG GAC AGC AAT (SEQ. ID. NO: 9) | CTG CAA TTC ATG GGC GTA TCT (SEQ. ID. NO: 10) |

Example 3

Induction of Mitogen-Activated Protein Kinase (MAPK) Activity by sCD93 Protein

To investigate molecular action involved in THP-1 cell differentiation, MAPK (mitogen-activated protein kinase) signaling pathway was investigated.

Figure 7:
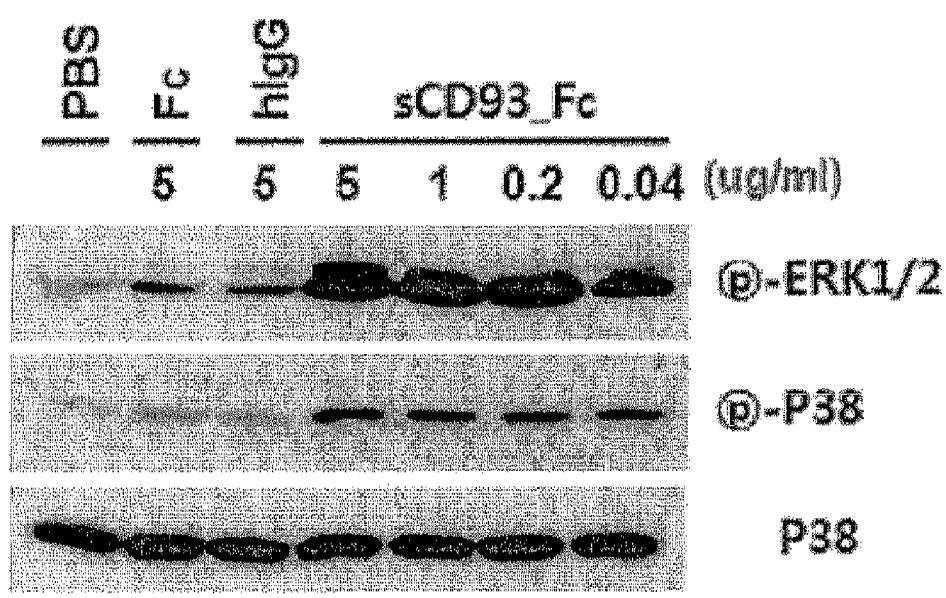
FIG. 7-FIG. 11 illustrate the effect of sCD93 protein on MAPK signal activation.

Particularly, negative control THP-1 cells were treated with PBS(−), 5 μg/ml of Fc, and 5 μg/ml of hIgG. Positive control THP-1 cells were treated with 0.1 μg/ml of PMA. Experimental group THP-1 cells were treated with sCD93_Fc at the different concentrations of 5, 1, 0.2, and 0.04 μg/ml. They were stayed in 37 incubator for 30 minutes after the treatment. Then, the cells were lysed by lysis buffer, followed by Western blotting. For the blotting, phospho-Erk 1/2 (cell signaling) and phospho-p38 (cell signaling) were used as primary antibodies (cell signaling), and total-p38 (cell signaling) was used for quantification. As a result, it was confirmed that phospho-Erk 1/2 and phospho-p38 were increased by sCD93_Fc dose dependently (FIG. 7).

Figure 8:
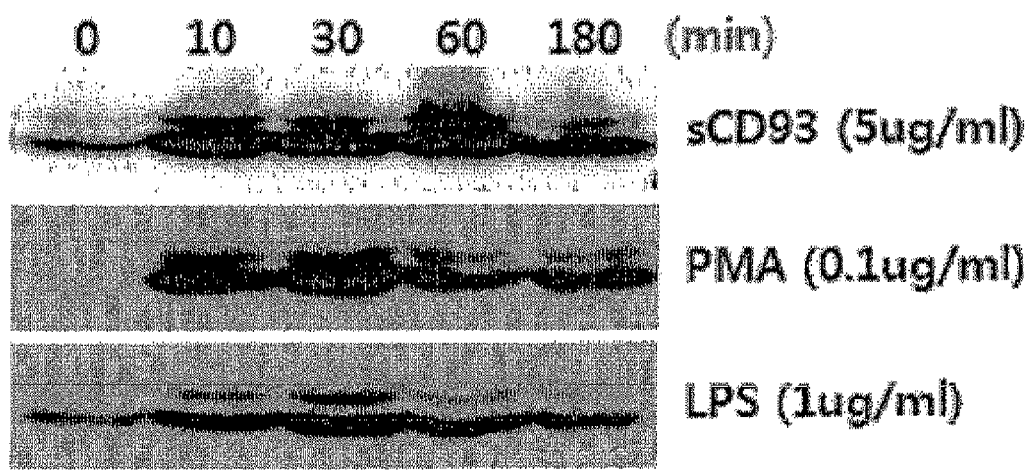

To observe changes of phosphor-Erk 1/2 level over the time, THP-1 cells were treated with 5 μg/ml of sCD93_Fc for 0, 10, 30, 60, and 180 minutes respectively by the same manner as described above, followed by Western blotting. Positive control THP-1 cells were treated with 0.1 μg/ml of PMA and 1 μg/ml of LPS by the same manner as described above, followed by Western blotting. From 10 minutes after the treatment of sCD93_Fc, phospho-Erk 1/2 level began to increase and when 30 minutes passed, the increase reached top. From 60 minutes after the treatment, the level began to slightly decrease (FIG. 8).

To investigate cytokine changes according to THP-1 differentiation and MAPK signaling changes, expressions of various pro-inflammatory cytokines were measured at RNA level. Particularly, negative control THP-1 cells were treated with PBS(−) and 5 μg/ml of hIgG. Positive control THP-1 cells were treated with 0.1 μg/ml of PMA. In the meantime, experimental group THP-1 cells were treated with sCD93_Fc. 24 hours later, LPS was treated thereto to investigate LPS susceptibility. 24 hours after the treatment, RNA was extracted and purified (Qiagen RNA miniprep kit). 1 μg of the purified RNA proceeded to reverse transcription (iScript cDNA synthesis kit, Bio-Rad) to synthesize cDNA.

TABLE 2

Primer sequence

| Cytokine | Forward | Reverse |
|---|---|---|
| IL-6 | TGG CTG AAA AAG ATG GAT GCT (SEQ. ID. NO: 11) | TCT GGC TTG TTC CTC ACT ACT (SEQ. ID. NO: 12) |
| IL-12 | TGT ACC AGG TGG AGT TCA AGA (SEQ. ID. NO: 13) | GGA GGA TTT TTG TGG CAC AGT (SEQ. ID. NO: 14) |
| iNOS | ATC TTG CCT GGG GTC CAT TAT (SEQ. ID. NO: 15) | CCT GGC CAG ATG TTC CTC TAT (SEQ. ID. NO: 16) |
| CXCL11 | CCT GGG GTA AAA GCA GTG AAA (SEQ. ID. NO: 17) | TTG CTT GCT TCG ATT TGG GAT (SEQ. ID. NO: 18) |
| CLEC4A | TTG GCA AGA CAG TGA GAA GGA (SEQ. ID. NO: 19) | AAT GTC GCT GAC CTT CTG GAT (SEQ. ID. NO: 20) |
| SPHK-1 | CTG TAG GAA GAG TGG GTT CCA (SEQ. ID. NO: 21) | GTG CCA GGA CTA GCA CAA AG (SEQ. ID. NO: 22) |
| IL-1β | ACA GCT GGA GAG TGT AGA TCC (SEQ. ID. NO: 23) | TTT TCT GCT TGA GAG GTG CTG (SEQ. ID. NO: 24) |
| TNF-α | TAG CCC ATG TTG TAG CAA ACC (SEQ. ID. NO: 25) | AGA GGA CCT GGG AGT AGA TGA (SEQ. ID. NO: 26) |

Next, changes of TNF-α expression at protein level was investigated according to THP-1 cell differentiation and MAPK signaling changes.

Figure 12:
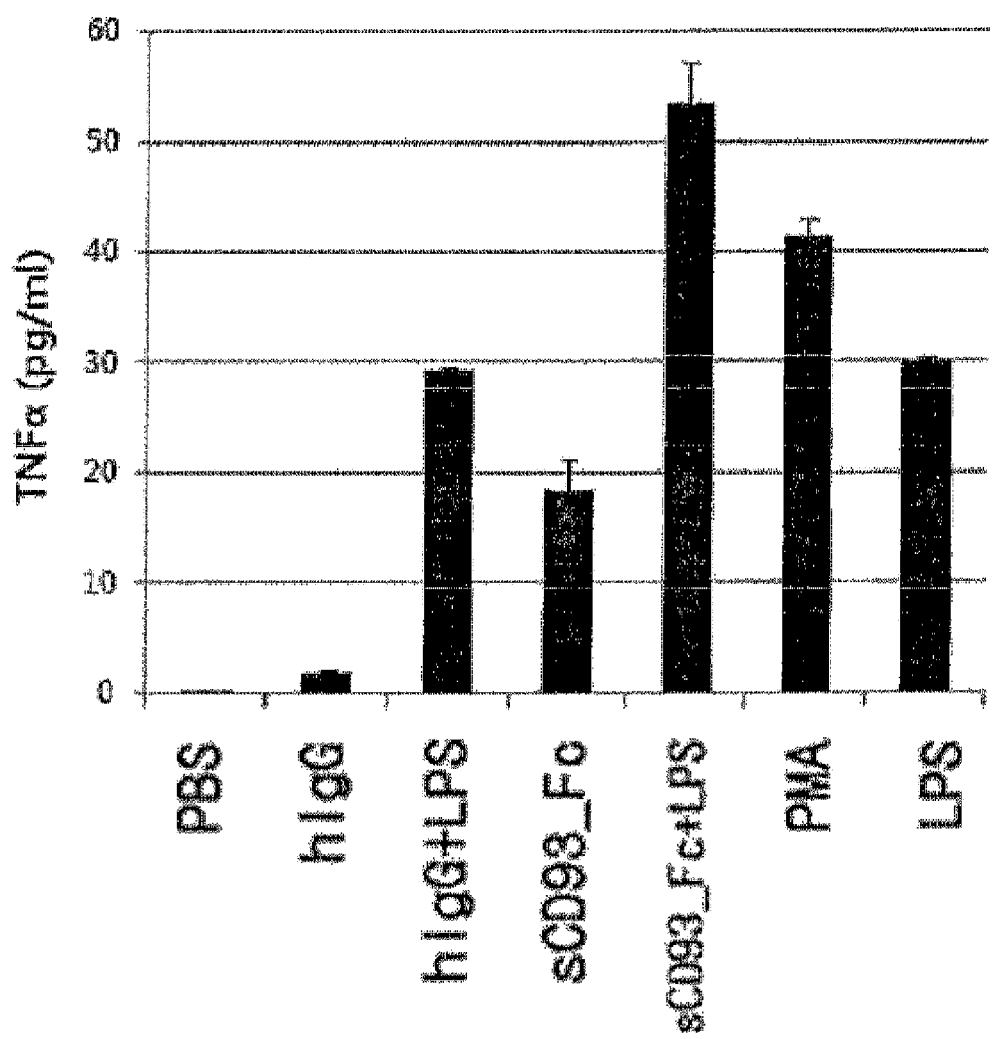
FIG. 12 is a graph illustrating the expression of TNF-α measured at protein level after the treatment of sCD93 protein.

Particularly, negative control THP-1 cells were treated with PBS(−) and 5 μg/ml of hIgG. Positive control THP-1 cells were treated with 0.1 μg/ml of PMA. In the meantime, experimental group THP-1 cells were treated with sCD93_Fc. 24 hours later, LPS was treated thereto to investigate LPS susceptibility. 24 hours after the LPS treatment, TNF-α level in the culture supernatant was measured by using Quantikine TNF-a assay kit (R&D system). As a result, TNF-α was slightly increased in the experimental group treated with sCD93_Fc alone, while TNF-α was significantly increased in the experimental group treated with both sCD93_Fc and LPS together. This result indicates that THP-1 cells were differentiated to macrophages by the treatment of sCD93_Fc with increasing susceptibility to TLR signal (FIG. 12).

Example 4

Induction of Matrix Metalloproteinase (MMP) Expression by sCD93 Protein

Effect of sCD93_Fc on matrix metalloproteinase (MMP) expression in THP-1 cells was investigated. Particularly, negative control THP-1 cells were treated with 5 µg/ml of hIgG, while positive control THP-1 cells were treated with 0.1 µg/ml of PMA. In the meantime experimental group THP-1 cells were treated with sCD93_Fc at the different concentrations of 5, 1, and 0.2 µg/ml. 24 hours after the treatment, Gelatin Zymography assay was performed to investigate expressions of MMP9 (92 kDa) and MMP-2 (72 kDa) in the culture supernatant. The supernatant obtained from 24 hour culture was electrophoresed on 8% SDS-PAGE gel containing 2 mg/ml of gelatin (Sigma). Then, the gel was stained with Coomassie blue. The gel was destained with destaining solution, followed by taking pictures.

Figure 13:
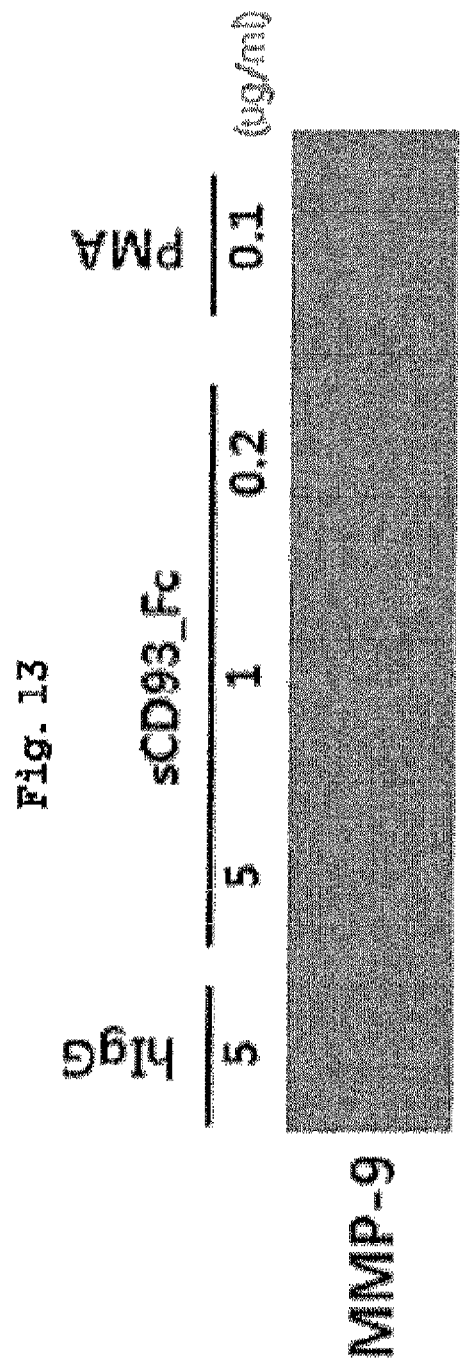
FIG. 13 is an electrophoresis photograph illustrating the effect of sCD93 protein on the expression of matrix metalloprotease (MMP).

As a result, MMP-9 level was increased by the treatment of sCD_Fc dose-dependently (FIG. 13).

Example 5

Induction of Phagocytosis by sCD93 Protein

Figure 14:
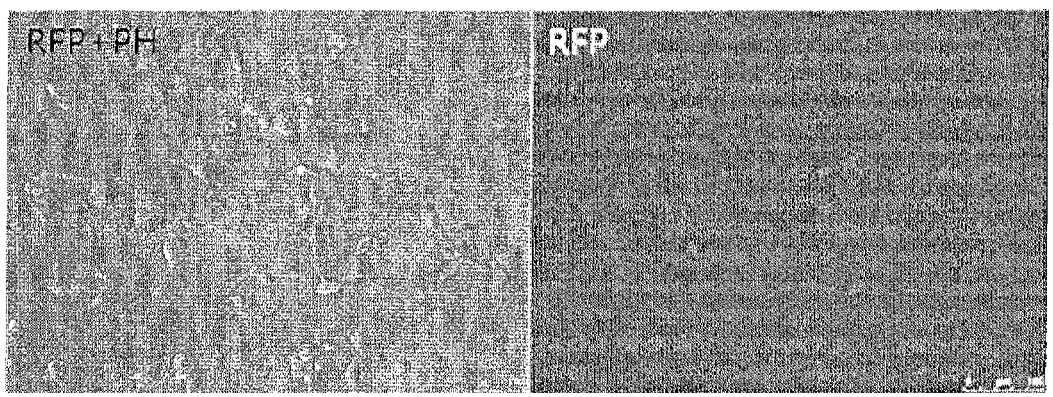
FIG. 14 is a set of photographs illustrating the inducing effect of sCD93 protein on phagocytosis.
Figure 15:
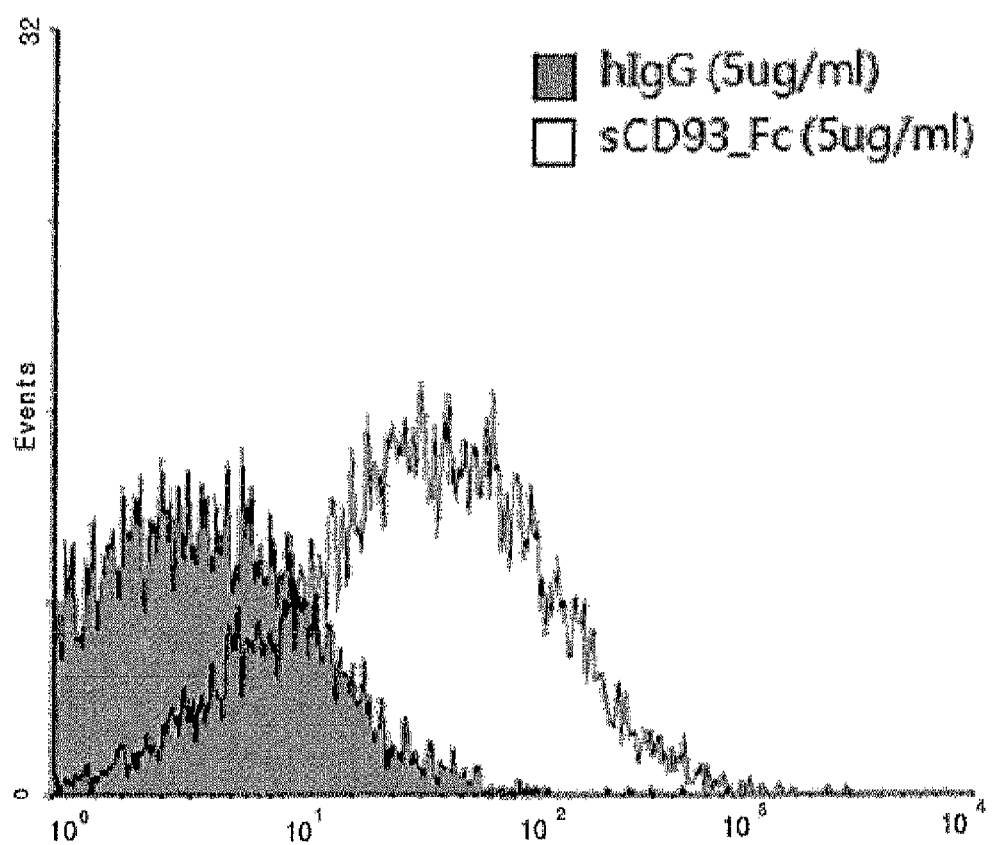
FIG. 15 is a FACS graph illustrating the inducing effect of sCD93 protein on phagocytosis.

Phagocytosis was measured using *E. coli* expressing mRFP to investigate phagocytosis activity according to the differentiation of THP-1 cells to macrophage-like cells. Particularly, THP-1 cells were treated with 5 µg/ml of sCD93_Fc, followed by culture for 3 days. Pre-cultured *E. coli* transformed with RFP (red fluorescent protein) expression vector were added to the differentiated THP-1 cells. 12 hours later, phagocytosis of *E. coli* by THP-1 cells was confirmed under fluorescent microscope (FIG. 14). Those cells were isolated by using cell dissociation buffer (EDTA buffer), which proceeded to FACS (Coolter) (FIG. 15).

As a result, phagocytosis in the differentiated cells by the treatment of sCD93_Fc was far greater with showing fluorescence than in the negative control cells treated with hIgG.

Example 6

Inhibition of TNF-α Production by CD93 Protein Antibody

Figure 16:
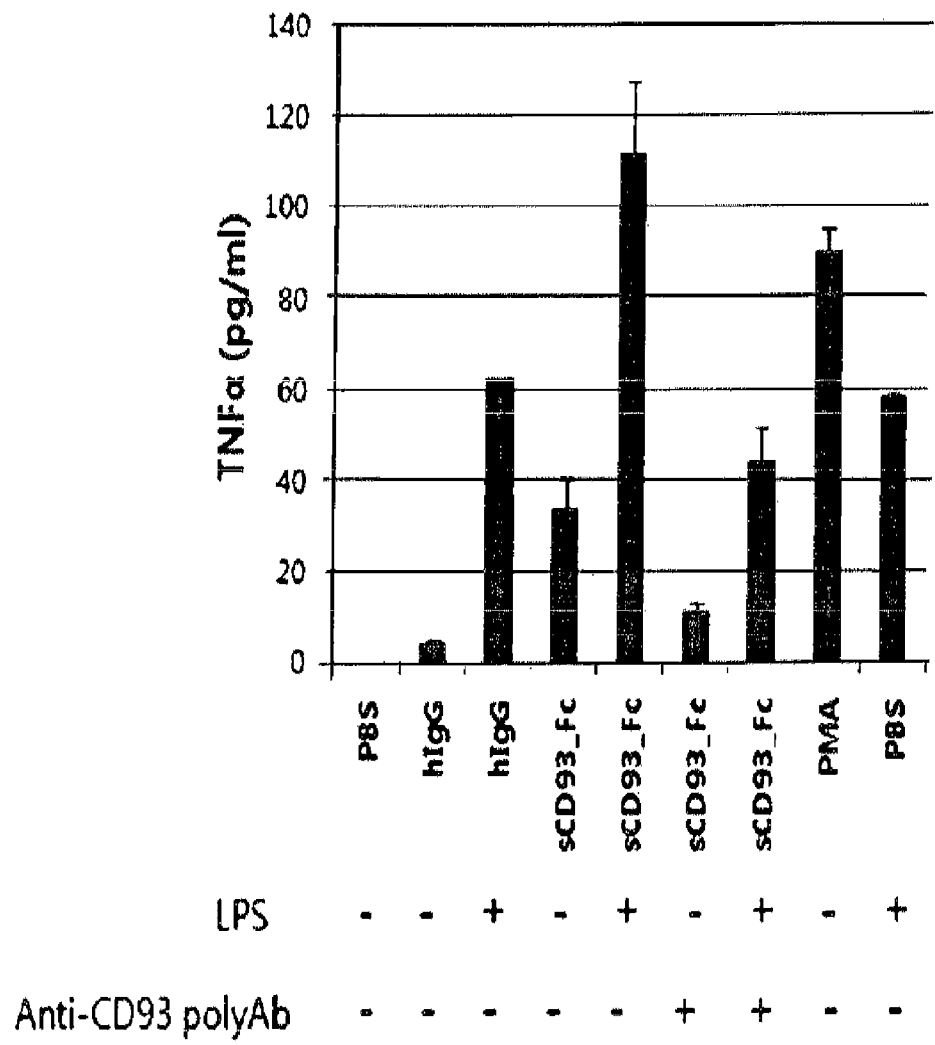
FIG. 16 is a graph illustrating the inhibitory effect of anti-CD93 antibody on the production of TNF-α.

To investigate the possibility of development of an anti-inflammatory agent using the antibody against sCD93_Fc based on its effect on inflammation and differentiation, THP-1 cells were treated with anti-CD93 antibody, and the effect on inflammation and differentiation was examined (FIG. 16). Particularly, negative control THP-1 cells were treated with PBS(−) and 5 µg/ml of hIgG. Positive control THP-1 cells were treated with 0.1 µg/ml of PMA. In the meantime, experimental group THP-1 cells were treated with 5 µg/ml of sCD93_Fc and 10 µg/ml of anti-CD93 polyclonal antibody (R&D system). 24 hours later, 1 µg/ml of LPS was treated thereto to investigate LPS susceptibility. 24 hours after the LPS treatment, the amount of TNF-α in the culture supernatant was measured by suing Quantikine TNF-a assay kit (R&D system).

As a result, the amount of TNF-α was slightly increased in the experimental group treated with sCD93_Fc alone. In the meantime, TNF-α level was higher in the experimental group treated with both sCD93_Fc and LPS together than in the experimental group treated with LPS alone. However, the treatment of anti-CD93 antibody inhibited such increase of TNF-α at least 50~60%.

Example 7

Expressions of Various Pro-Inflammatory Cytokines Investigated by Using siRNA

CD93 in THP-1 was knock-downed by using CD93 siRNA, and changes of various cytokines were investigated by real-time PCR.

First, $2 \times 10^5$ THP-1 cells (medium: 10% FBS (Hyclone)+ RPMI1640 (Hyclone)) were distributed in 24-well plate, to which 1 ul of Lipofectamine RNAiMax (Invitrogen) and 10 pmol of CD93 siRNA (siCD93, Bioneer) were added, which stood for 10 minutes to induce transfection of the THP-1 cells. For negative control, negative control siRNA (Bioneer) was used. For positive control, full-length CD93 (CD93_Full) gene (Kugi, hMU003993, Kugi No. IRAT-49-A06) was used, followed by transfection by the same manner as described above. The cells were cultured for 12 hours in $CO_2$ incubator, followed by LPS treatment. The cells were cultured for 12 more hours. Real-time PCR was performed with TNF-α and IL-6 by the same manner as described in Examples 2 and 3.

Figure 17:
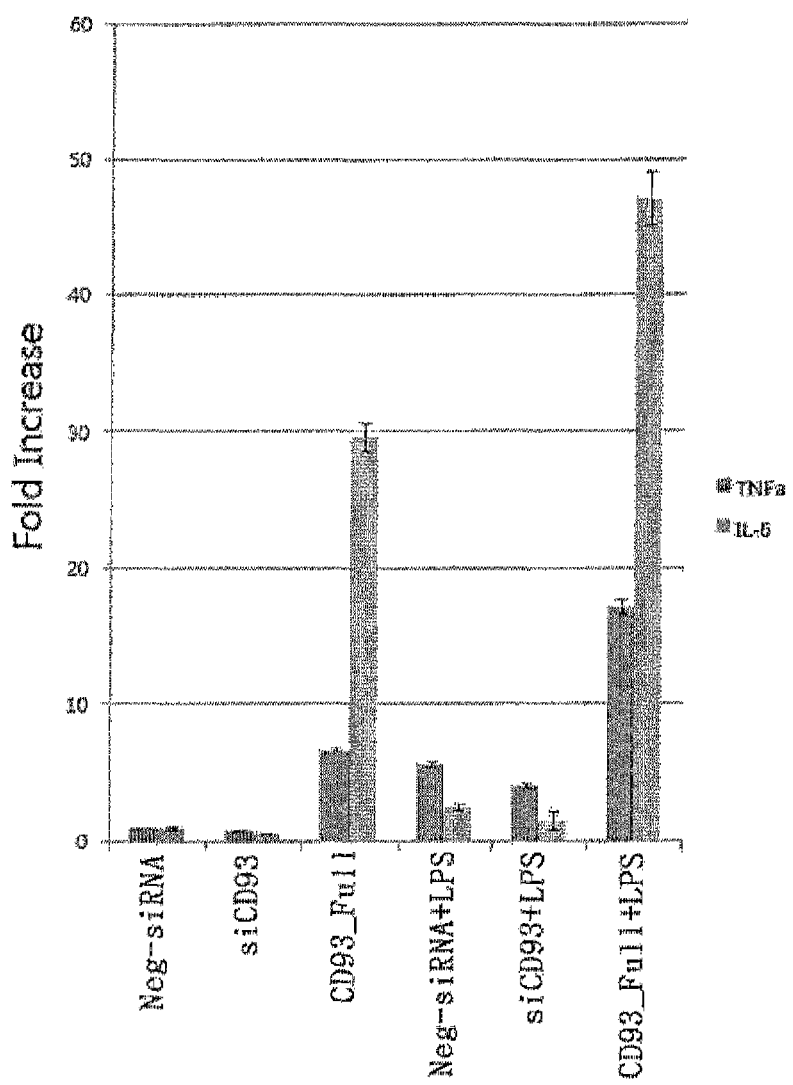
FIG. 17 is a graph illustrating the inhibitory effect of CD93 siRNA on the productions of TNF-α and IL-6.

As a result, levels of the two pro-inflammatory cytokines TNF-α and IL-6 were decreased by the treatment of siCD93. The increase by LPS treatment was also decreased. On the other hand, the levels of TNF-α and IL-6 were increased in the experiment group treated with CD93_Full. The levels of TNF-α and IL-6 were more increased by the treatment of LPS (FIG. 17).

Example 8

CD93 Expression and CD93 Soluble Fragment Level in THP-1 Cells, the Human Mononuclear Cells To investigate the expression of CD93 and its fragmentation by various inflammation inducing substances or under inflammation environment, CD93 expression in THP-cells, the human mononuclear cells, and CD93 soluble fragment level in the culture supernatant were measured.

<8-1> CD93 Expression in THP-1 Cells, the Human Mononuclear Cells: FACS

THP-1 cells were cultured in RPMI 1640 supplemented with 10% FBS, penicillin G (100 IU/ml), streptomycin (100 µg/ml), L-glutamine (2 mM), HEPES (10 mM), and sodium pyruvate (1.0 mM) in a 37 incubator. The cultured THP-1 cells were treated with PBS, LPS (1.0 µg/ml), TNF-α (0.5 µg/ml) or PMA (0.1 µg/ml) for 24 hours, followed by fixation in 4% paraformaldehyde for 20 minutes. After washing with PBS once, blocking was performed with 3% NGS (normal goat serum) for 30 minutes, followed by washing three times. The cells were reacted with ice-cold goat anti-human CD93 antibody (R&D systems) for 1 hour. After washing with PBS three times again, the cells were reacted with ice-cold anti-goat IgG-FITC antibody for 1 hour for fluorescence staining. Control groups were treated with anti-CD14-FITC antibody respectively for fluorescence staining. The stained cells were analyzed by flow cytometry (EPICS Elite, Coulter).

Figure 18:
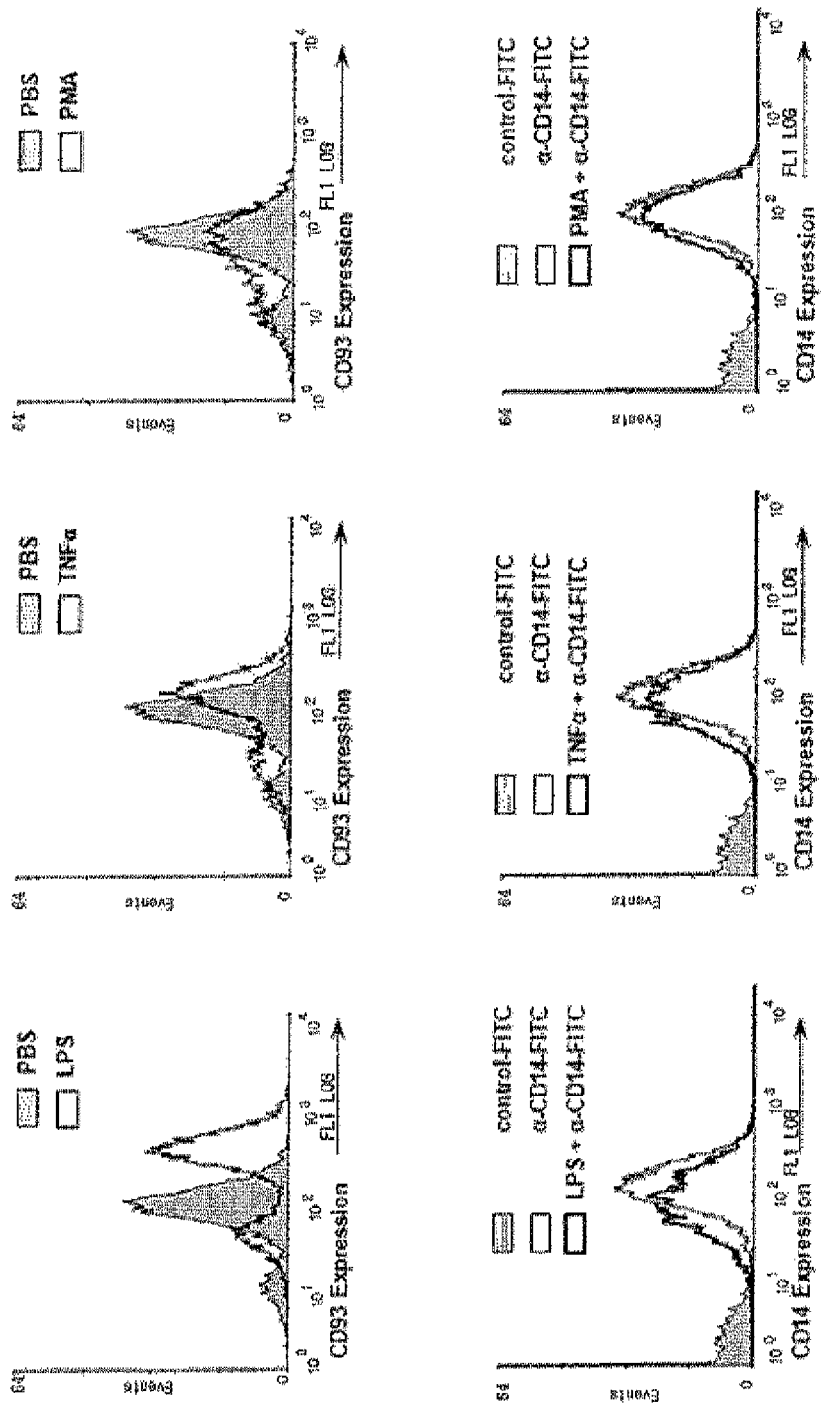
FIG. 18 is a set of graphs illustrating the expression of CD93 on the cell surface after treating THP-1 cells (human mononuclear cells) with LPS, TNF-α or PMA, measured by FACS.

As a result, as shown in FIG. 18, CD93 expression on the cell surface of THP-1 was increased by LPS and TNF-α but hardly increased by PMA (FIG. 18). The expression of CD14 used for the control group on the cell surface was decreased by LPS, TNF-α, and PMA, which was assumed to be attributed to CD14 fragmentation. CD14 fragmentation has been known as an important mechanism in down-modulation of monocyte-macrophage activation (Schutt, C. 1999. Cd14. *Int. J. Biochem. Cell Biol.* 31:545. 23. Le-Barillec, K., M. Si-Tahar, V. Balloy, and M. Chignard. 1999. Proteolysis of monocyte CD14 by human leukocyte elastase inhibits lipopolysaccharide-mediated cell activation. *J. Clin. Invest.* 103:1039. Bazil, V., and J. L. Strominger. 1991. Shedding as a mechanism of down-modulation of CD14 on stimulated human monocytes. *J. Immunol.* 147:1567). According to many previous research results, collagenase, neutrophil elastase, and cathepsin G can induce fragmentation of CD14 on cell surface (Bryniarski, K., K. Maresz, M. Szczepanik, M. Ptak, and W. Ptak. 2003. Modulation of macrophage activity by proteolytic enzymes. Differential regulation of IL-6 and reactive oxygen intermediates (ROIs) synthesis as a possible homeostatic mechanism in the control of inflammation. *Inflammation* 27:333. Le-Barillec, K., M. Si-Tahar, V. Balloy, and M. Chignard. 1999. Proteolysis of monocyte CD14 by human leukocyte elastase inhibits lipopolysaccharide-mediated cell activation. *J. Clin. Invest.* 103:1039. Coyne, C. P., T. Howell III, H. Smodlaka, C. Willetto, B. W. Fenwick, and E. Chenney. 2002. Alterations in membrane-associated CD14 expression and the simultaneous liberation of soluble CD14 fragment in adherent macrophages mediated by a leukocyte carboxyl/aspartate protease. *J. Endotoxin. Res.* 8:273.).

<8-2> Western Blotting

THP-1 cells were cultured in RPMI 1640 supplemented with 10% FBS, penicillin G (100 IU/ml), streptomycin (100 μg/ml), L-glutamine (2 mM), HEPES (10 mM), and sodium pyruvate (1.0 mM) in a 37 incubator. After treating the cultured THP-1 cells with PBS, LPS (1.0 μg/ml), TNF-α (0.5 μg/ml) or PMA (0.1 μg/ml) for 24 hours, lysate and supernatant were obtained. The samples were boiled for 5 minutes and frozen for storage. After loading the samples on 8% SDS-PAGE gel, electrophoresis was performed. The gel was transferred onto nitrocellulose membrane, followed by blocking with 4% skim milk. The gel was reacted with goat anti-CD93 antibody (0.5 μg/ml, R&D systems) at room temperature for 1 hour. After washing with PBST three times, the gel was reacted with anti-goat IgG-HRP antibody (0.5 μg/ml, Santa Cruz) at room temperature for 1 hour. As internal controls, anti-β actin (Santa Cruz) and anti-goat IgG-HRP (Santa Cruz) were used. Experiment was performed using ECL kit (ECL Plus, Amersham, USA) according to the manufacturer's instructions.

Figure 19:
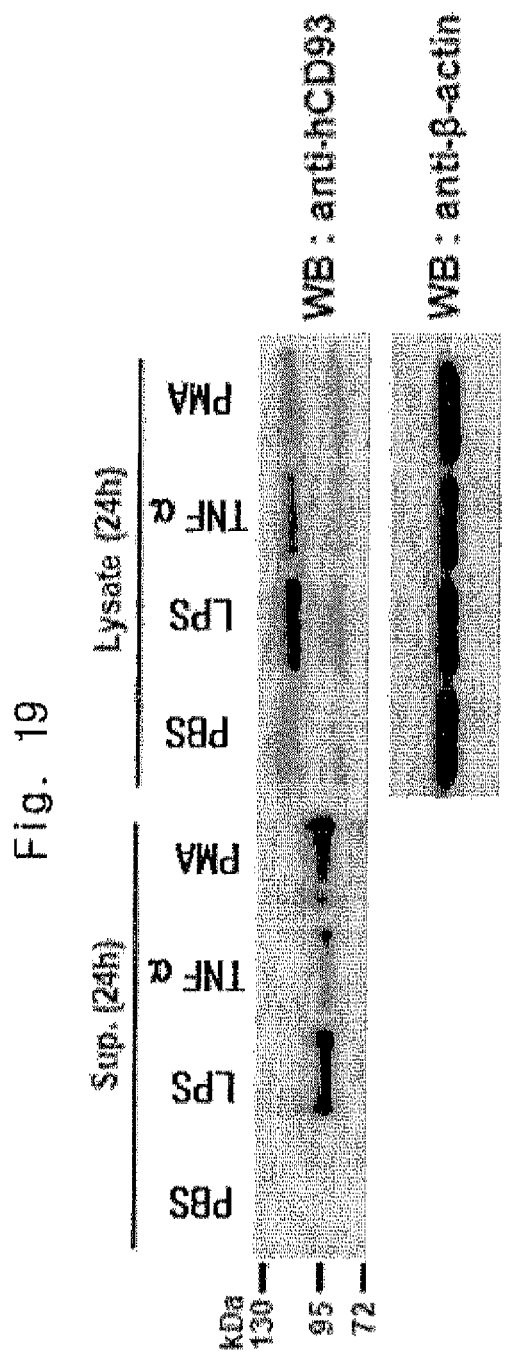
FIG. 19 is a set of photographs illustrating the expressions of CD93 and its soluble fragment on the cell surface after treating THP-1 cells with LPS, TNF-α or PMA, measured by Western blotting.

As a result, as shown in FIG. 19, the expression of CD93 itself was increased by the treatment of LPS and TNF-α, which was consistant with the result of FACS, but it was not increased by the treatment of PMA. In the meantime, the expression of CD93 soluble fragment was increased by the treatment of LPS, TNF-α and even PMA (FIG. 19). The above results indicate that not only CD93 itself but also CD93 soluble fragment are up-regulated in inflammation condition or by inflammation inducing substances in THP-1 and Jukat cells. Therefore, CD93 or its soluble fragment is expected to be an effective diagnostic marker for inflammatory disease.

<8-3> RT-PCR

THP-1 cells were cultured in 6 well-plate, and then treated with PBS, LPS (1.0 μg/ml, InvivoGen), and PMA (0.1 μg/ml, Sigma) respectively. 24 hours after the treatment, RNA was identified by using RNA identification kit (Qiagen). For reverse transcription, reverse transcriptase (Bio-Rad) and dNTP were mixed, leading to reaction for one hour at to obtain cDNA of each. For real-time PCR, CFX96 system (Bio-Rad) was used. PCR was performed as follows: predenaturation at 95 for 3 minutes, annealing at 95 for 15 seconds, polymerization at 60 for 1 minute, 40~45 cycles. Fluorescence was measured at each annealing stage and data was recorded automatically stage by stage. Particularly, 2 μl of cDNA template and CD93 primer were mixed with 23 iQ SYBR Supermix (Bio-Rad) for reaction. Every reaction was repeated twice. To measure the relative mRNA expression, average threshold cycle (Ct) value was set as standard value. Every Ct value was standardized by GAPDH. Primer sets used herein are as follows: CD93: forward primer CTC TGG GGC TAC TGG TCT ATC (SEQ. ID. NO: 34), reverse primer TGT CGG ACT GTA CTG GTT CTC (SEQ. ID. NO: 35); GAPDH: forward primer CAT GTT CGT CAT GGG TGT GAA (SEQ. ID. NO: 36), reverse primer GGA CTG TGG TCA TGA GTC CTT (SEQ. ID. NO: 37).

Figure 20:
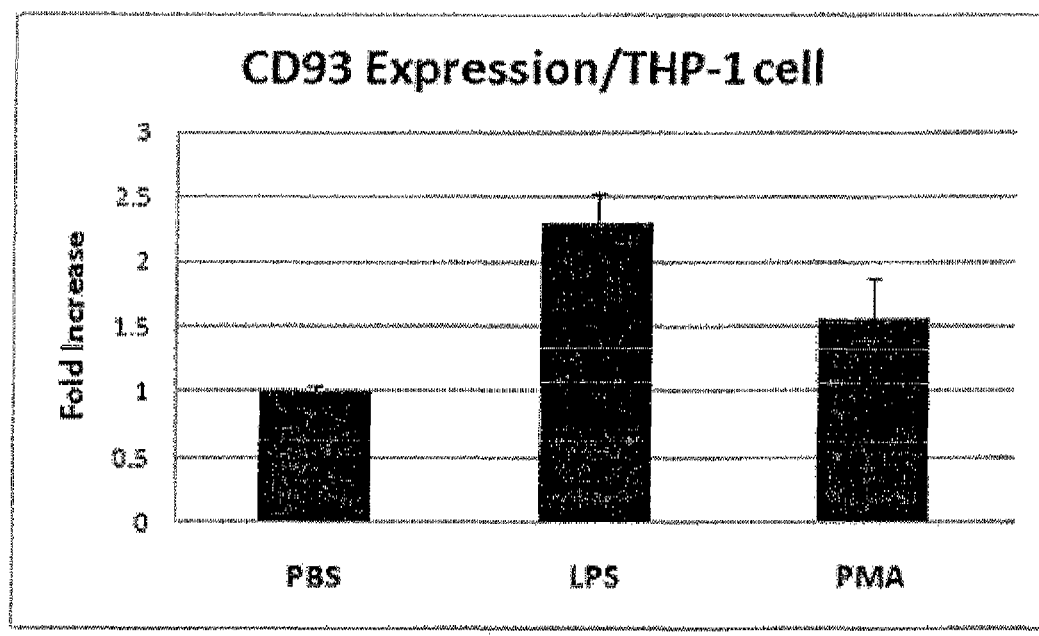
FIG. 20 is a graph illustrating the expression of CD93 mRNA on the cell surface after treating THP-1 cells with LPS or PMA, measured by RT-PCR.

As a result, as shown in FIG. 20, CD93 expression in THP-1 cells was significantly increased by the treatment of LPS and PMA (FIG. 20).

Example 9

CD93 Expression in Mouse Peripheral Blood Mononuclear Cells and Peritoneal Cells and Quantification of CD93 Soluble Fragment in Serum and Peritoneal Lavage Fluid (In Vivo)

Like the above in vitro quantification of CD93 expression, in vivo experiment was performed as follows to investigate CD93 expression and fragmentation thereof. Particularly, peritonitis was induced in the test mouse or inflammation inducing substance (thioglycollate or LPS) was injected to the mouse. Then, CD93 expression in the mouse peripheral blood mononuclear cells and peritoneal cells was investigated and at the same time the amount of CD93 soluble fragment in serum and peritoneal lavage fluid (PLF) was measured.

<9-1> CD93 Expression in Mouse Peripheral Blood Mononuclear Cells and Peritoneal Cells: FACS Balb/c mice at 6 weeks of age were injected with 1 ml of PBS, 4% thioglycollate or 0.1 mg/ml of LPS. Three days later, blood was drawn from retro-orbital vein of the mice using heparin-coated glass capillary tube. Then, serum and PBMC cells were obtained by centrifugation. After scarifying the mice, peritoneal lavage fluid (PLF) and peritoneal cells (mostly intraabdominal macrophages) were obtained from the abdominal cavity. To eliminate red blood cells from the cells, 10 ml of red blood cell lysing buffer (Sigma) was added, followed by reaction twice at 37, resulting in the complete elimination of red blood cells. Fluorescence staining was performed by the same manner as described in Example <8-1>. At that time, anti-mouse CD93 antibody (R&D systems) and anti-goat IgG-FITC (Santa Cruz) were used. To investigate macrophage differentiation, double staining was performed by using CD11b antibody (BD Sciences), the differentiation marker.

Figure 21:
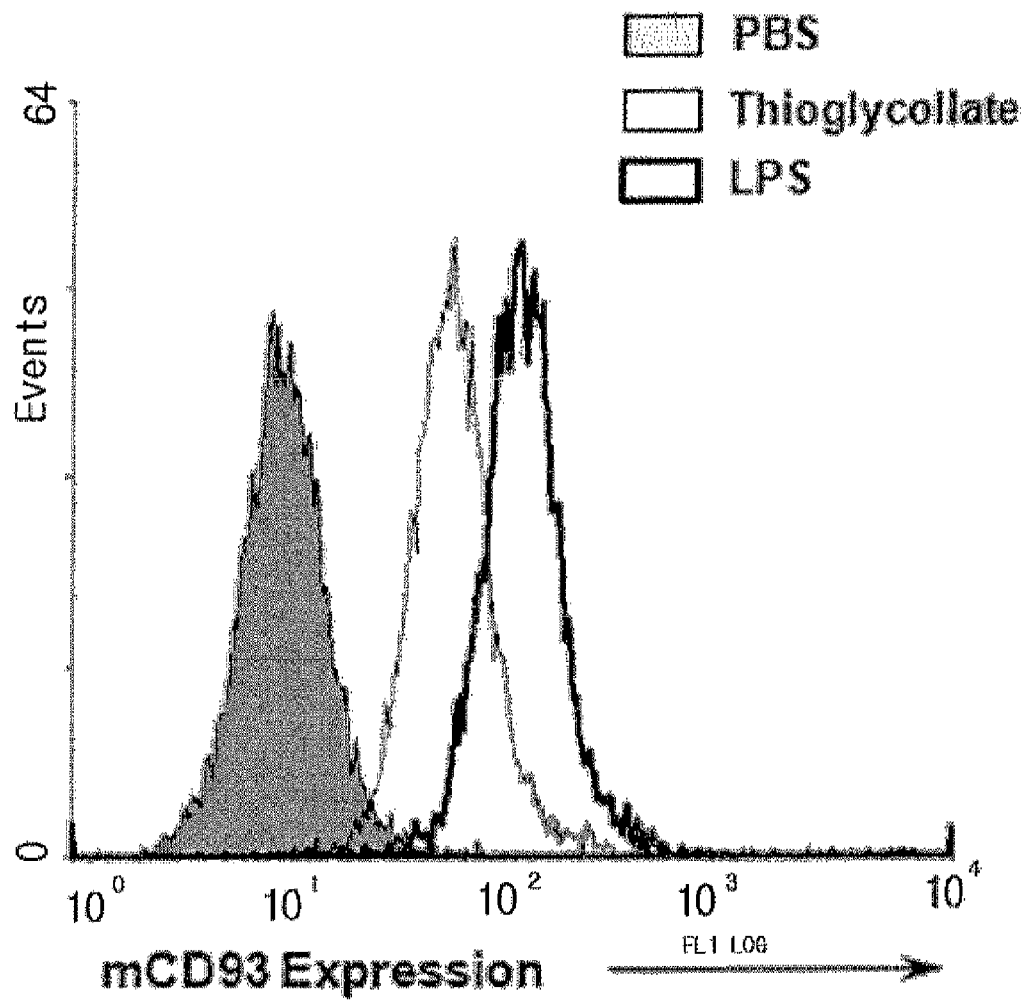
FIG. 21 is a graph illustrating the expression of mouse CD93 in peritoneal macrophages after injecting PBS, thioglycollate or LPS to a mouse, analyzed by FACS.

As a result, as shown in FIG. 21, CD93 expression in macrophages of peritoneal cells of the mouse was significantly increased by the treatment of LPS. The expression was similarly increased by the treatment of thioglycollate (FIG. 21). Therefore, it was confirmed that macrophages existing in PBMCs were moved into peritoneal fluid by the treatment of thioglycollate and LPS.

<9-2> Western Blotting

The remaining half of the cells not used in Example <9-1> was lysed, followed by Western blotting. Western blotting was performed by the same manner as described in Example <8-2> except that sheep anti-mouse CD93 antibody (R&D systems) and anti-sheep IgG-HRP (Santa Cruz) were used to detect mouse CD93. To investigate macrophage differentiation, double staining was performed by using CD11b antibody (BD Sciences), the differentiation marker. As internal controls, anti-β actin (Santa Cruz) and anti-goat IgG-HRP (Santa Cruz) were used. Experiment was performed using ECL kit (ECL Plus, Amersham, USA) according to the manufacturer's instructions.

Figure 22:
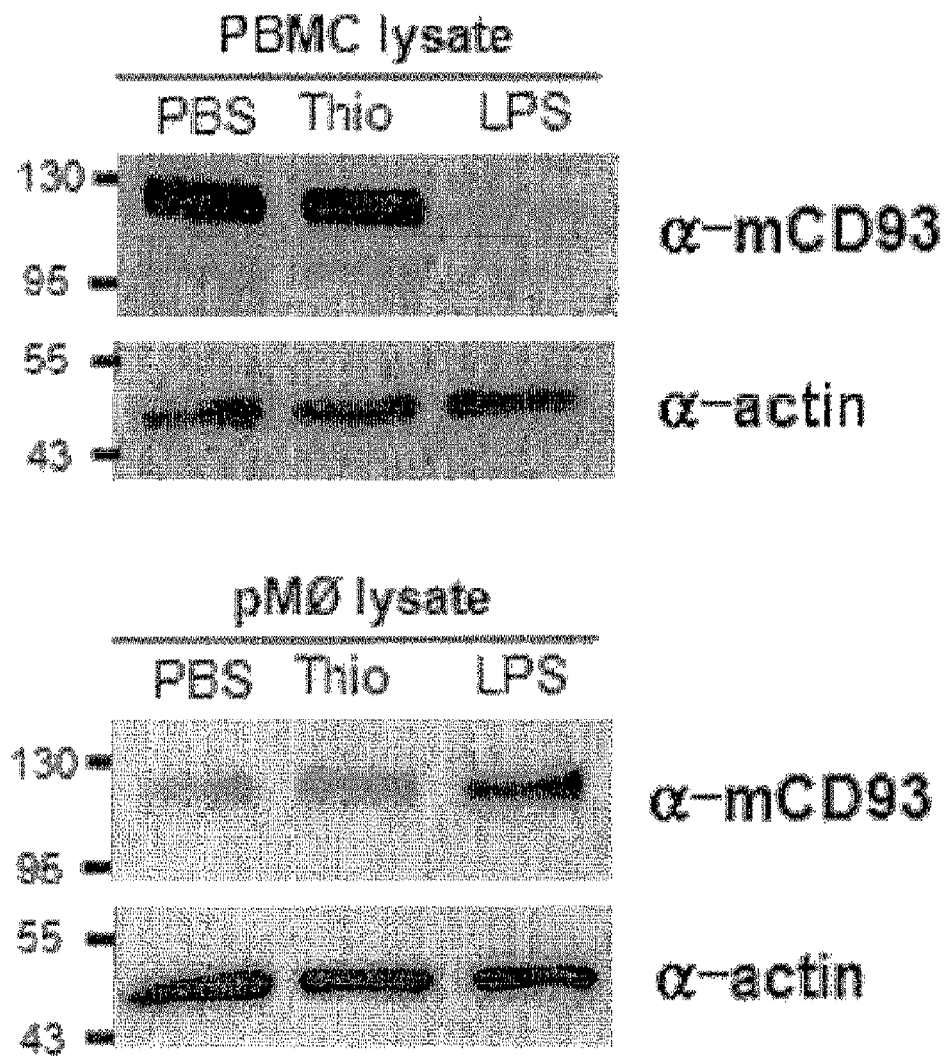
FIG. 22 is a set of photographs illustrating the expressions of mouse CD93 in PBMC and peritoneal macrophages after injecting PBS, thioglycollate or LPS to a mouse, observed by Western blotting.

As a result, as shown in FIG. 22, CD93 expression was significantly increased in mouse peritoneal cells by the treatment of thioglycollate and LPS (FIG. 22), which was consistent with the result of FACS above.

<9-3> Quantification of CD93 Soluble Fragment: Sandwich ELISA

After confirming by FACS and Western blotting that the amount of CD93 molecule itself was increased, the inventors further investigated the changes of CD93 soluble fragment. Particularly, the amount of CD93 soluble fragment in serum and peritoneal lavage fluid (PLF) was measured by sandwich ELISA.

First, 93-well falcon plate (Becton Dickinson) was coated with rat anti-mouse CD93 antibody (R&D Systems) at the concentration of 100 ng/well for overnight. After washing the plate with PBST three times, blocking was performed with 3% skim milk at room temperature for 30 minutes. After washing the plate with PBST three times again, each of mouse serum and peritoneal lavage fluid was loaded thereto (100 µl/well), which stood for 2 hours. As standard material for quantification, mouse CD93 soluble fragment was used. After washing the plate 3 times, 1 µg/ml of sheep anti-mouse CD93 antibody (R&D systems) was added thereto, which stood for 1 hour. One µg/ml of anti-sheep IgG-HPR antibody (Santa Cruz) was added thereto, followed by reaction for 1 hour. After washing the plate with PBST three times again, color development was induced by using OPD (Sigma). OD was measured by suing spectrophotometer (VERSAmax tunable microplate reader, Molecular Devices). Absolute quantification was performed with the measured value using standard curve.

Figure 23:
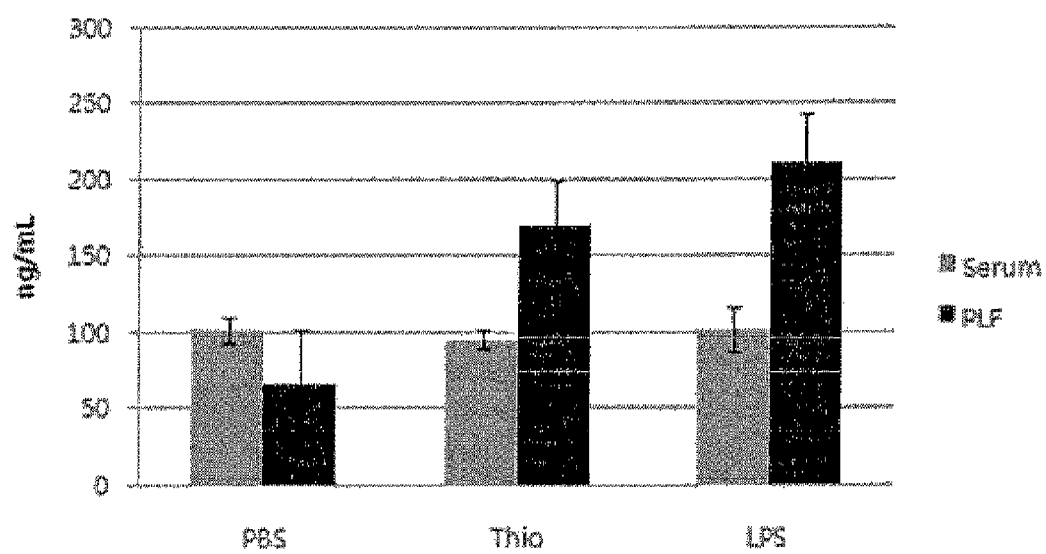
FIG. 23 is a graph illustrating the amount of mouse CD93 soluble fragment in serum and peritoneal lavage fluid after injecting PBS, thioglycollate or LPS to a mouse, measured by sandwich ELISA.

As a result, as shown in FIG. 23, the amount of CD93 soluble fragment in serum was hardly changed by the treatment of LPS or thioglycollate. However, the amount of CD93 soluble fragment in peritoneal lavage fluid was significantly increased by the treatment of LPS or thioglycollate (FIG. 23). Therefore, it was suggested that CD93 soluble fragment could be effectively used as a diagnostic marker for inflammatory disease.

Example 10

CD93 Expression in Synovial Membrane Tissue and Quantification of CD93 Soluble Fragment in Synovial Fluid <10-1> CD93 Expression in Synovial Membrane Tissue: Immunohistochemistry Synovial membrane (synovium) tissues were obtained from three rheumatoid-arthritis (RA) patients and 2 osteo-arthritis (OA) patients, which were fixed in 4% paraformaldehyde for overnight. The tissues were dehydrated with alcohol and embedded in paraffin, followed by sectioning. To eliminate peroxidase activity therein, the tissues were reacted with methanolic $H_2O_2$. To eliminate non-specific reaction, blocking was performed with 3% NGS (normal goat serum for 2 hours. The tissues were reacted with goat anti-human CD93 antibody (R&D), viotinylated anti-goat IgG, and streptavidine-peroxidase complex (Vector, Peterborough, UK) stepwise for 1 hour each. The tissues were counter-stained with hematoxyline, followed by observation under Olympus microscope (Tokyo, Japan).

Figure 24:
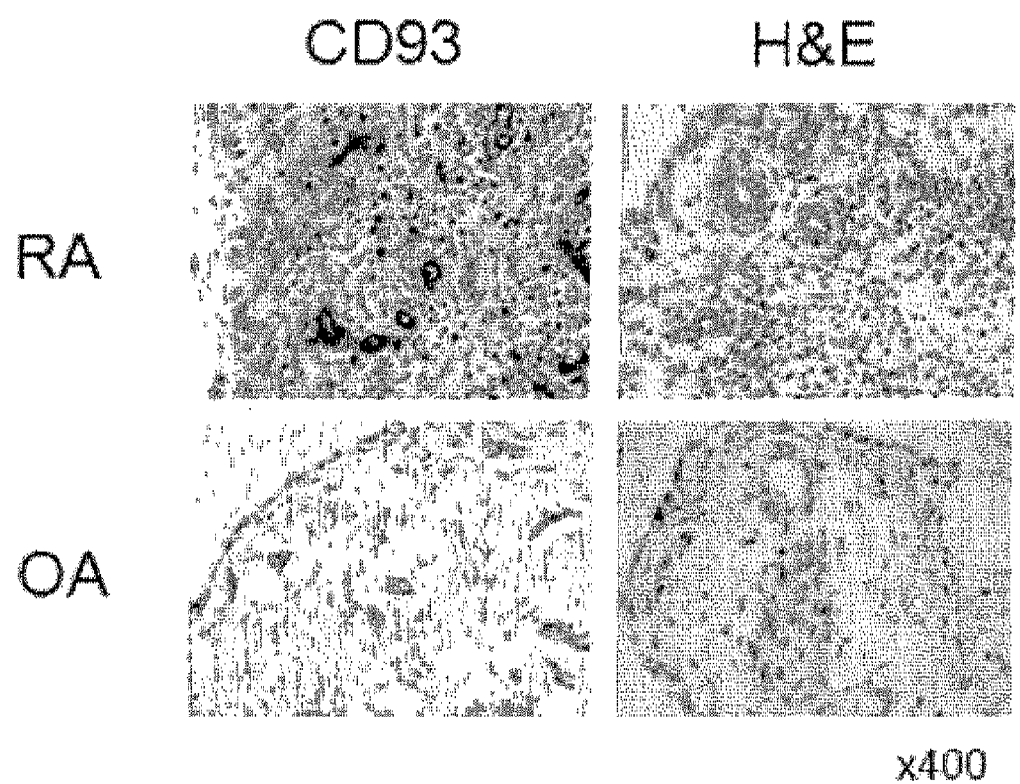
FIG. 24 is a set of photographs illustrating the expression of CD93 in synovial membrane tissue obtained from a patient with rheumatoid arthritis (RA) or degenerative arthritis (OA), analyzed by immunohistochemical technique after staining the tissue with anti-CD93 antibody.

As a result, as shown in FIG. 24, CD93 up-regulation was more significant in synovial membrane tissues obtained from rheumatoid arthritis patients than in synovial membrane tissues from osteo-arthritis patients (FIG. 24). Particularly, CD93 expression was significantly increased in synovial lining where lymphocytes are infiltrated, sublining, and perivascular region.

<10-2> Quantification of CD93 Soluble Fragment in Synovial Fluid: Sandwich ELISA The amount of CD93 soluble fragment in synovial fluid obtained from 8 rheumatoid arthritis patients and 8 osteo-arthritis patients was measured by sandwich ELISA.

First, 93-well falcon plate (Becton Dickinson) was coated with rat anti-human CD93 antibody (R&D Systems) at the concentration of 100 ng/well for overnight. After washing the plate with PBST three times, blocking was performed with 3% skim milk at room temperature for 30 minutes. After washing the plate with PBST three times again, each of synovial fluid (SF) obtained from 8 rheumatoid arthritis patients and osteo-arthritis patients was loaded thereto (100 µg/well), which stood for 2 hours. As standard material for quantification, human soluble CD93 was used. After washing the plate with 3 times, 1 µg/ml of goat anti-human CD93 antibody (R&D systems) was added thereto, which stood for 1 hour. One µg/ml of anti-goat IgG-HPR antibody (Santa Cruz) was added thereto, followed by reaction for 1 hour. After washing the plate with PBST three times again, color development was induced by using OPD (Sigma). OD was measured by suing spectrophotometer. Absolute quantification was performed with the measured value using standard curve.

Figure 25:
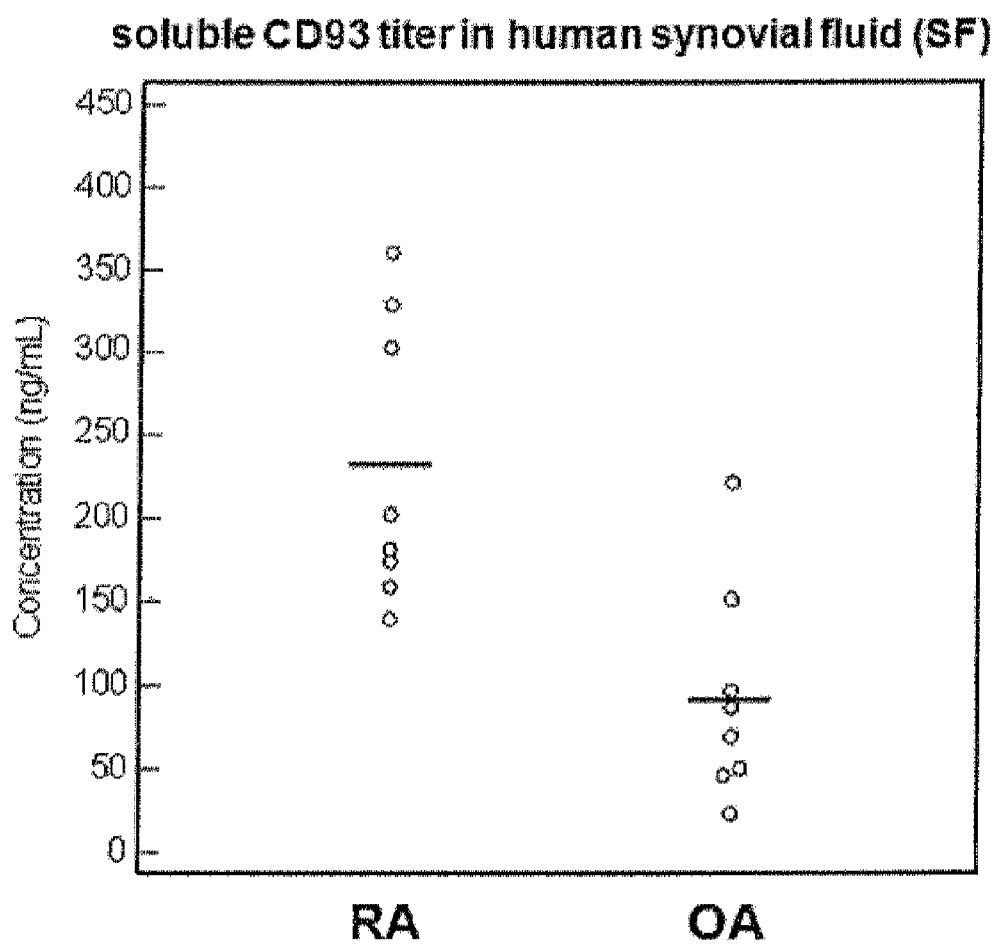
FIG. 25 is a graph illustrating the amount of CD93 soluble fragment in synovial fluid obtained from a patient with rheumatoid arthritis (RA) or degenerative arthritis (OA), measured by sandwich ELISA.

As a result, as shown in FIG. 25, the amount of CD93 soluble fragment in synovial fluid obtained from rheumatoid arthritis patients was significantly higher than that in synovial fluid obtained from osteo-arthritis patients (FIG. 25).

Therefore, it was suggested that CD93 molecule or its soluble fragment could be effectively used as a diagnostic marker for inflammatory disease.

INDUSTRIAL APPLICABILITY

As explained hereinbefore, the present invention can be effectively used for the development of a therapeutic agent and a diagnostic kit for various inflammatory diseases.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for diagnosing rheumatoid arthritis comprising:
   coating proteins from a biological sample obtained from synovial fluid and a control on a fixture;
   inducing an antigen-antibody reaction by adding an antibody specifically binding to a CD93 soluble fragment to the above fixture;
   detecting the antigen-antibody reaction product produced by the above antigen-antibody reaction by using a secondary antibody conjugate marker and chromogenic substrate solution;
   comparing the detection results between the biological sample and the control; and
   diagnosing rheumatoid arthritis or high risk of rheumatoid arthritis when CD93 soluble fragment is up-regulated in the biological sample, compared with the level in the control,
   wherein the antigen-antibody reaction product is measured by a sandwich ELISA.

2. The method according to claim 1, wherein the fixture is selected from the group consisting of nitrocellulose membrane, PVDF membrane (polyvinylidene difluoride membrane), 96-well plate made of polyvinyl resin or polystylene resin, and glass side glass.

3. The method according to claim 1, wherein the secondary antibody conjugate marker is selected from the group consisting of HRP (horseradish peroxidase), alkaline phosphatase, colloid gold, FITC (poly L-lysine-fluorescein isothiocyanate), RITC (rhodamine-B-isothiocyanate), and dye.

4. The method according to claim 1, wherein the chromogenic substrate solution is the one selected from the group consisting of TMB (3,3',5,5'-tetramethyl bezidine), ABTS [2,2'-azino-bis(3-ethylbenzothiazoline-6-sulfonic acid)], and OPD (o-phenylenediamine).

5. The method according to claim 1, wherein the soluble fragment is the 95 kDa ectodomain of CD93 protein released after cell culture.

6. The method according to claim 1, wherein the soluble fragment has the amino acid sequence of SEQ ID NO:1.

* * * * *